US011338010B2

(12) United States Patent
Goren et al.

(10) Patent No.: US 11,338,010 B2
(45) Date of Patent: May 24, 2022

(54) SYSTEMS, METHODS, AND KITS FOR DIAGNOSTICS AND TREATMENT OF VIRAL RESPIRATORY INFECTION

(71) Applicant: SUZHOU KINTOR PHARMACEUTICALS, INC., Suzhou (CN)

(72) Inventors: Ofer A. Goren, Irvine, CA (US); John McCoy, Irvine, CA (US)

(73) Assignee: SUZHOU KINTOR PHARMACEUTICALS, INC., Suzhou (CN)

( * ) Notice: Subject to any disclaimer, the term of this patent is extended or adjusted under 35 U.S.C. 154(b) by 0 days.

(21) Appl. No.: 15/929,788

(22) Filed: May 21, 2020

(65) Prior Publication Data

US 2021/0299207 A1    Sep. 30, 2021

Related U.S. Application Data

(60) Provisional application No. 62/704,531, filed on May 14, 2020, provisional application No. 62/704,416, (Continued)

(51) Int. Cl.
| | |
|---|---|
| A61K 31/445 | (2006.01) |
| A61K 31/553 | (2006.01) |
| A61K 31/4427 | (2006.01) |
| A61K 31/4164 | (2006.01) |
| A61K 31/4152 | (2006.01) |
| A61K 31/16 | (2006.01) |
| A61K 38/08 | (2019.01) |
| A61P 31/14 | (2006.01) |
| A61K 31/573 | (2006.01) |
| A61K 31/198 | (2006.01) |
| A61K 31/473 | (2006.01) |
| A61K 31/05 | (2006.01) |
| A61K 31/167 | (2006.01) |
| A61K 31/4184 | (2006.01) |
| A61K 31/122 | (2006.01) |
| A61K 31/4155 | (2006.01) |
| A61K 31/337 | (2006.01) |
| A61K 9/00 | (2006.01) |
| A61K 31/4166 | (2006.01) |
| A61K 31/58 | (2006.01) |
| A61K 31/155 | (2006.01) |
| A61K 31/277 | (2006.01) |
| A61K 31/437 | (2006.01) |
| A61K 31/4439 | (2006.01) |
| A61K 31/4709 | (2006.01) |
| A61K 31/57 | (2006.01) |
| A61K 33/18 | (2006.01) |
| A61K 38/09 | (2006.01) |
| A61K 45/06 | (2006.01) |
| C07K 14/71 | (2006.01) |

(Continued)

(52) U.S. Cl.
CPC ........... *A61K 38/08* (2013.01); *A61K 9/0019* (2013.01); *A61K 9/0053* (2013.01); *A61K 31/05* (2013.01); *A61K 31/122* (2013.01); *A61K 31/155* (2013.01); *A61K 31/167* (2013.01); *A61K 31/198* (2013.01); *A61K 31/277* (2013.01); *A61K 31/337* (2013.01); *A61K 31/4155* (2013.01); *A61K 31/4164* (2013.01); *A61K 31/4166* (2013.01); *A61K 31/4184* (2013.01); *A61K 31/437* (2013.01); *A61K 31/4439* (2013.01); *A61K 31/473* (2013.01); *A61K 31/4709* (2013.01); *A61K 31/57* (2013.01); *A61K 31/573* (2013.01); *A61K 31/58* (2013.01); *A61K 33/18* (2013.01); *A61K 38/09* (2013.01); *A61K 45/06* (2013.01); *A61P 31/14* (2018.01); *C07K 14/71* (2013.01); *C07K 16/2827* (2013.01); *C12N 15/1136* (2013.01); *C12N 2310/11* (2013.01)

(58) Field of Classification Search
CPC .............. A61K 31/445; A61K 31/4427; A61K 31/4164; A61K 31/4152; A61K 31/16; A61K 31/573
USPC ........ 514/327, 341, 391, 404, 618, 628, 629
See application file for complete search history.

(56) References Cited

U.S. PATENT DOCUMENTS

| | | | |
|---|---|---|---|
| 9,730,948 B2 * | 8/2017 | Farman | A61P 27/02 |
| 2009/0029924 A1 | 1/2009 | Strongin et al. | |

(Continued)

FOREIGN PATENT DOCUMENTS

| | | |
|---|---|---|
| WO | 2006031922 A2 | 3/2006 |
| WO | 2011088474 A2 | 7/2011 |

OTHER PUBLICATIONS

Goren, A., et al., A preliminary observation: "Male pattern hair loss among hospitalized COVID-19 patients in Spain—A potential clue to the role of androgens in COVID-19 severity", Journal of Cosmetic Dermatology, vol. 19, No. 7, Apr. 2020, pp. 1545-1547.

(Continued)

*Primary Examiner* — Raymond J Henley, III
(74) *Attorney, Agent, or Firm* — Parker Highlander PLLC

(57) ABSTRACT

Systems, methods, and kits for treating, preventing, and diagnosing viral infection using an androgen mediated pathway are described. Additionally, methods and kits for guiding treatment of viral respiratory disease are described by a method for testing for polymorphisms in the androgen receptor gene. Further, systems and methods for treatment of viral respiratory disease with various anti-androgens is detailed. Finally, systems, methods, and kits for treating, preventing, and diagnosing SARS-CoV-2 (COVID-19) are presented.

25 Claims, No Drawings

Related U.S. Application Data filed on May 8, 2020, provisional application No. 62/704,126, filed on Apr. 22, 2020, provisional application No. 63/004,398, filed on Apr. 2, 2020, provisional application No. 63/004,171, filed on Apr. 2, 2020, provisional application No. 63/001,629, filed on Mar. 30, 2020.

(51) Int. Cl.
*C07K 16/28* (2006.01)
*C12N 15/113* (2010.01)

(56) References Cited

U.S. PATENT DOCUMENTS

| | | |
|---|---|---|
| 2011/0206727 A1 | 8/2011 | Leclerc |
| 2016/0272707 A1 | 9/2016 | Levine et al. |
| 2017/0065540 A1 | 3/2017 | Dunman et al. |
| 2017/0128465 A1 | 5/2017 | Atlschul et al. |
| 2019/0209469 A1* | 7/2019 | Patel ............ A61K 9/0053 |

OTHER PUBLICATIONS

Yin-Chum Yam, L. et al., Corticosteroid treatment of severe acute respiratory syndrome in Hong Kong, Journal of Infection, Academic Press, London, GB, vol. 54, No. 1, Dec. 2006, pp. 28-39.

Nielsen H.C., et al., "Dihydrotestosterone Inhibits Fetal Rabbit Pulmonary Surfactant Production", The Journal of Clinical Investigation, vol. 69, No. 3, Mar. 1982, pp. 611-616.

International Search Report and Written Opinion for PCT/US2021/019201, filed Feb. 23, 2021, dated Jun. 11, 2021.

International Search Report and Written Opinion for PCT/US2021/024814, filed Mar. 30, 2021, dated Jul. 13, 2021.

* cited by examiner

SYSTEMS, METHODS, AND KITS FOR DIAGNOSTICS AND TREATMENT OF VIRAL RESPIRATORY INFECTION

CROSS-REFERENCE TO RELATED APPLICATIONS

This application is related to and claims the benefit of U.S. Provisional Application No. 63/001,629, titled Systems, Methods and Kits for Diagnostics and Treatment of SARS-CoV-2, filed on Mar. 30, 2020, U.S. Provisional Application No. 63/004,171, titled Systems, Methods and Kits for Diagnostics and Treatment of Viral Respiratory Infection, filed on Apr. 2, 2020, U.S. Provisional Application No. 63/004,398, titled Systems, Methods and Kits for Diagnostics and Treatment of Viral Respiratory Infection, filed on Apr. 2, 2020, U.S. Provisional Application No. 62/704,126, titled Systems, Methods and Kits for Diagnostics and Treatment of Viral Respiratory Infection, filed on Apr. 22, 2020, U.S. Provisional Application No. 62/704,416, titled Systems, Methods and Kits for Diagnostics and Treatment of Viral Respiratory Infection, filed on May 8, 2020, and U.S. Provisional Application No. 62/704,531, titled Systems, Methods and Kits for Diagnostics and Treatment of Viral Respiratory Infection, filed on May 14, 2020, the entire contents of each being incorporated herein by reference.

FIELD

The present invention relates to system, methods, and kits for treating, preventing, and diagnosing viral infection using an androgen mediated pathway. The present invention relates to methods and kits for predicting viral respiratory disease severity. Additionally, the present invention relates to methods and kits for guiding treatment of viral respiratory disease by testing for polymorphisms in the androgen receptor gene or genes under regulatory control of the androgen receptor. Similarly, the following invention relates to systems and methods for treatment of viral respiratory disease with various anti-androgens including, but not limited to, androgen receptor antagonists, androgen synthesis inhibitors, or antigonadotropins. Additionally, the present systems, methods, and kits are useful for treating, preventing, and diagnosing coronavirus, e.g., SARS-CoV-2 (COVID-19).

BACKGROUND

In late 2019, a novel coronavirus, subsequently named SARS-CoV-2 (COVID-19), was first reported in Hubei province in China. Since it was first reported, a worldwide pandemic has ensued affecting more than 450,000 individuals as of March 2020. In the midst of the pandemic, epidemiological reports unveiled a disproportionate low rate of severe cases among adult females compared to adult males, 42% and 58%, respectively. Similarly, the rate of severe cases among pre-pubescent children was exceptionally low at 0.6% (See Guan W J, Ni Z Y, Hu Y, Liang W H, Ou C Q, et al. Clinical Characteristics of Coronavirus Disease 2019 in China. N Engl J Med. 2020). An explanation for the skewed prevalence of severe COVID-19 infection in adult males has yet to be elucidated.

In newborns, it has long been recognized that male infants are more susceptible to respiratory distress syndrome (See Torday J S, Nielsen H C, Fend Mde M, Avery M E. Sex differences in fetal lung maturation. Am Rev Respir Dis. 1981; 123(2): 205-208) and less likely to respond to prenatal glucocorticoid therapy to protect against respiratory distress. Respiratory distress is intimately tied to the production of pulmonary surfactant, e.g., pulmonary surfactant proteins have been demonstrated to protect against influenza A (See Hartshorn K L, Crouch E C, White M R, Eggleton P, Tauber A I, Chang D, Sastry K. Evidence for a Protective Role of Pulmonary Surfactant Protein D (SP-D) Against Influenza A Viruses. J Clin Invest. 1994; 94 (1): 311-319). In animal studies, it was demonstrated that a sexual dimorphism in fetal pulmonary surfactant production is influenced by the androgen receptor (AR) (See Nielsen H C. Androgen receptors influence the production of pulmonary surfactant in the testicular feminization mouse fetus. J Clin Invest. 1985; 76(1): 177-181). For example, in rabbits, dihydrotestosterone was shown to inhibit fetal pulmonary surfactant production in both males and females while an anti-androgen, flutamide, was demonstrated to remove the sexual dimorphism in surfactant production.

While severe COVID-19 symptoms are primarily manifested in older adults, the similar sexual dimorphism in the severity of respiratory disease is of interest. In addition, AR expression is low prior to pubertal maturation and may contribute to the low incidence of severe COVID-19 infection in children. The lower rate of severe COVID-19 infection in female patients may be attributed to lower androgen receptor expression.

SUMMARY

Systems, methods, and kits are disclosed herein for diagnosing and treating viral respiratory infection by first measuring polymorphisms in the androgen receptor gene or polymorphisms in genes under regulatory control of the androgen receptor. Identification of polymorphisms in the androgen receptor gene can be used to guide treatments of viral respiratory disease. Treatments for viral respiratory disease may include, but are not limited to, androgen receptor antagonists, androgen synthesis inhibitors, or antigonadotropins. Specifically, the present systems, methods, and kits are useful for treating, preventing, and diagnosing viral respiratory disease as a result of coronavirus infection, e.g., SARS-CoV-2 (COVID-19).

In an exemplary embodiment, a composition administered to a subject having or suspected of having a viral respiratory infection includes any one or combination of: an androgen receptor antagonists or anti-androgen; an androgen synthesis inhibitor; an agent that counters the effect of androgens; a globulin (SHBG) stimulator; an antigonadotropin; a mineralocorticoid to suppress androgen production in the adrenal gland; a glucocorticoid to suppress androgen production in the adrenal gland; an insulin sensitizing medication; and a vaccine or an immunogen against androstenedione that reduces the level of testosterone or increases estrogen.

In some embodiments: the anti-androgen is any one or combination of: cyproterone acetate, megestrol acetate, chlormadinone acetate, spironolactone, medrogestone, oxendolone, osaterone, bifluranol acetate, finasteride, dutastride, flutamide, bicalutamide, nilutamide, topilutamide, enzalutamide, apalutamide, dienogest, drospirenone, medrogestone, nomegestrol acetate, promegestone, trimegestone, ketoconazole, abiraterone acetate, seviteronel, aminoglutethimide, epristeride, alfaestradiol, isotretinoin, saw palmetto, marijuana, cannabinoids, darolutamide, EZN-4176, AZD-3514, and AZD-5312, apatorsen, galeterone, ODM-2014, TRC-253, BMS-641988, proxalutamid, Luteinizing hormone-releasing hormone (LH-RH), follicle-stimulating hormone (FSH), triptorelin pamoate, docetaxel, diethylstilbestrol, tadalafil, silodosin, tamsulosin hydrochloride, naftopidil, solifenacin succinate, tamsulosin, tamsulosin hydrochloride, alfuzosin hydrochloride, prazosin hydrochloride, doxazosin, doxazosin mesylate, solifenacin succinate, allylestrenol, benzydamine hydrochloride, cefatrizine, chlormadinone acetate, flavoxate hydrochloride, gestonorone caproate, indoramin hydrochloride, mepartricin, oxybutynin chloride, phenoxybenzamine hydrochloride, terazosin, terazosin hydrochloride, or degarelix. The agent that counters the effect of androgens is a sex hormone-binding globulin (SHBG) stimulator. The glucocorticoid is anticorticotropin. The insulin sensitizing medication is metformin.

In some embodiments, the composition is formulated to facilitate administration of the composition topically to the skin, nasally, sub-lingually, orally, by injection (e.g., intramuscular, intravenous, subcutaneous, depot), via inhalation, or ocular application.

In some embodiments, the viral respiratory infection is any one or combination of coronavirus, influenza, influenza A, influenza B, SARS-CoV-1, SARS-CoV-2, MERS-CoV, or rhinoviruses.

In some embodiments, the compositions is formulated to alter androgen receptor function and subsequently down stream genes under regulatory control of the androgen receptor.

In some embodiments, the down stream genes include any one or combination of angiotensin converting enzyme 2 (ACE2), furin, and transmembrane protease serine 2 (TMPRSS2).

In some embodiments, the composition is formulated to block the production of proteins in the lung so as to alter viral entry into cells or to bolster host immunity.

In some embodiments, the anti-androgen is combined with any one or combination of an anti-inflammatory agent, an anti-bacterial agent, or aspartame.

In some embodiments, the composition is formulated for use as a treatment of the viral respiratory infection, a therapy for the viral respiratory infection, a prophylactic for the viral respiratory infection, a preventive measure for contracting the viral respiratory infection, a diagnosis of a type of viral respiratory infection, a prediction for respiratory disease severity of the viral respiratory infection, a prediction for determining an effective treatment or prophylactic composition, and/or a prediction for determining an effective administration dosage of the composition for use as a treatment or prophylactic.

In an exemplary embodiment, a method of using a composition on a subject having or suspected of having a viral respiratory infection involves administering a composition to a subject, the composition including any one or combination of: an androgen receptor antagonists or anti-androgen; an androgen synthesis inhibitor; an agent that counters the effect of androgens; a globulin (SHBG) stimulator; an antigonadotropin; a mineralocorticoid to suppress androgen production in the adrenal gland; a glucocorticoid to suppress androgen production in the adrenal gland; an insulin sensitizing medication; and vaccine or an immunogen against androstenedione that reduces the level of testosterone or increases estrogen.

In some embodiments: the anti-androgen is any one or combination of: cyproterone acetate, megestrol acetate, chlormadinone acetate, spironolactone, medrogestone, oxendolone, osaterone, bifluranol acetate, finasteride, dutastride, flutamide, bicalutamide, nilutamide, topilutamide, enzalutamide, apalutamide, dienogest, drospirenone, medrogestone, nomegestrol acetate, promegestone, trimegestone, ketoconazole, abiraterone acetate, seviteronel, aminoglutethimide, epristeride, alfaestradiol, isotretinoin, saw palmetto, marijuana, cannabinoids, darolutamide, EZN-4176, AZD-3514, and AZD-5312, apatorsen, galeterone, ODM-2014, TRC-253, BMS-641988, proxalutamid, Luteinizing hormone-releasing hormone (LH-RH), follicle-stimulating hormone (FSH), triptorelin pamoate, docetaxel, diethylstilbestrol, tadalafil, silodosin, tamsulosin hydrochloride, naftopidil, solifenacin succinate, tamsulosin, tamsulosin hydrochloride, alfuzosin hydrochloride, prazosin hydrochloride, doxazosin, doxazosin mesylate, solifenacin succinate, allylestrenol, benzydamine hydrochloride, cefatrizine, chlormadinone acetate, flavoxate hydrochloride, gestonorone caproate, indoramin hydrochloride, mepartricin, oxybutynin chloride, phenoxybenzamine hydrochloride, terazosin, terazosin hydrochloride, or degarelix. The agent that counters the effect of androgens is a sex hormone-binding globulin (SHBG) stimulator. The glucocorticoid is anticorticotropin. The insulin sensitizing medication is metformin.

In some embodiments, the administration of the composition involves any one or combination of topical application to the skin, nasal application, oral application, via injection, via inhalation, or ocular application.

In some embodiments, the viral respiratory infection is any one or combination of coronavirus, influenza, influenza A, influenza B, SARS-CoV-1, SARS-CoV-2, MERS-CoV or rhinoviruses.

In some embodiments, the method involves altering androgen receptor function and subsequently down stream genes under regulatory control of the androgen receptor.

In some embodiments, the down stream genes include any one or combination of angiotensin converting enzyme 2 (ACE2), furin, and transmembrane protease serine 2 (TMPRSS2).

In some embodiments, the method involves blocking the production of proteins in the lung so as to alter viral entry into cells or to bolster host immunity.

In some embodiments, the composition is use as a treatment of the viral respiratory infection, a therapy for the viral respiratory infection, a prophylactic for the viral respiratory infection, a preventive measure for contracting the viral respiratory infection, a diagnosis of a type of viral respiratory infection, a prediction for respiratory disease severity of the viral respiratory infection, a prediction for determining an effective treatment or prophylactic composition, and/or a prediction for determining an effective administration dosage of the composition for use as a treatment or prophylactic.

In some embodiments, the treatment involves administering the composition as a treatment for the viral respiratory infection and/or a prophylactic for the viral respiratory infection before, during, and/or after the subject is first diagnosed with the viral respiratory infection and/or before, during, and/or after the subject is hospitalized due to the viral respiratory infection.

In some embodiments, the method involves predicting anti-androgen treatment response via evaluation of a genetic variation of the androgen receptor (AR) gene.

In some embodiments, the method involves guiding selection of anti-androgen treatment and/or dosage selection of the selected anti-androgen treatment based on the predicted anti-androgen treatment response.

In some embodiments, the method involves predicting the anti-androgen treatment response involves measuring polymorphisms in the AR gene.

In some embodiments, the method involves predicting infection symptom severity, infection mortality, and/or whether the subject will need a ventilator or respiration due to the infection.

In some embodiments: the number of cytosine-adenine-guanine (CAG) repeats in the first exon of the AR gene, the number of guanine-guanine-(any nucleotide) (GGN) repeats in the first exon in the AR gene, and/or a ratio of CAG/GGN repeats is used as the genetic variant; and a cut off value for the number of CAG repeats the first exon of AR gene is used to define a person with androgen sensitivity.

In some embodiments, the cut-off value for the number of CAG repeats the first exon of AR gene is between 10 and 30.

In some embodiments, variants in the promoter region of the AR are used as the genetic variant.

In some embodiments, the method involves administering the composition routinely.

In some embodiments, the anti-androgen is combined with any one or combination of an anti-inflammatory agent, an anti-bacterial agent, or aspartame.

In an exemplary embodiment, a kit includes a deoxyribonucleic acid (DNA) sample collection unit configured to obtain a genetic sample via buccal swab, saliva sample, blood sample, tissue sample, and/or hair sample; a viral respiratory infection sensitivity unit configured to identify polymorphisms in the androgen receptor gene; and a DNA diagnostic assay.

In an exemplary embodiment, a method of identifying whether a person is at risk of mortality or developing severity of infection following viral respiratory infection involves determining the risk of severity or mortality of the viral respiratory infection by identifying and measuring promotor regions in any one or combination of the androgen receptor (AR) gene, the TMPRSS2 gene, the furin gene, or the ACE2 gene.

In some embodiments, the method involves predicting anti-androgen treatment response via evaluation of a genetic variation of the AR gene, the TMPRSS2 gene, the furin gene, or the ACE2 gene.

In some embodiments, the genetic variation includes any one or combination of: one or more of: F877L/T878A, F877L, T878A, rs137852591, rs104894742, rs1057518177, rs1057521121, rs1057521122, rs1057523747, rs1064793480, rs1064793645, rs1064794065, rs1064794069, rs1064795250, rs1085307685, rs1085307962, rs12014709, rs1204038, rs1337080, rs137852562, rs137852563, rs137852564, rs137852565, rs137852566, rs137852567, rs137852568, rs137852569, rs137852570, rs137852571, rs137852572, rs137852573, rs137852574, rs137852575, rs137852576, rs137852577, rs137852578, rs137852579, rs137852580, rs137852581, rs137852582, rs137852583, rs137852584, rs137852585, rs137852586, rs137852587, rs137852588, rs137852589, rs137852590, rs137852592, rs137852593, rs137852594, rs137852595, rs137852596, rs137852597, rs137852598, rs137852599, rs137852600, rs137852601, rs1800053, rs201934623, rs2361634, rs5031002, rs5918757, rs6152, rs6624304, rs750324117, rs754201976, rs755226547, rs759327087, rs864622007, rs869320731, rs869320732, rs878853033, rs886039558, rs886041050, rs886041128, rs886041129, rs886041130, rs886041131, rs886041132, rs886041133, rs886041352, rs9332969, or rs9332971; one or more of: rs12329760, rs2070788, rs383510, rs463727, rs34624090, rs55964536, rs734056, rs4290734, rs34783969, rs11702475, rs35899679, rs35041537, rs8134378, rs2070788, rs9974589, rs7364083, or rs2070788; one or more of: rs2285666, G8790A, rs35803318, rs1978124, rs2048683, rs2074192, rs2106809, rs2285666, rs233575, rs4240157, rs4646155, rs4646156, rs4646174, rs4646176, rs4646188, rs6632677, rs714205, or rs879922; or one or more of: rs17514846, rs2071410, rs4702, rs4932178, rs6226, or rs6227.

In an exemplary embodiment, a composition administered to a subject having or suspected of having a viral respiratory infection includes comprising dutasteride, wherein the composition is formulated for use as a treatment of the viral respiratory infection, a therapy for the viral respiratory infection, a prophylactic for the viral respiratory infection, a preventive measure for contracting the viral respiratory infection, a diagnosis of a type of viral respiratory infection, a prediction for respiratory disease severity of the viral respiratory infection, a prediction for determining an effective treatment or prophylactic composition, and/or a prediction for determining an effective administration dosage of the composition for use as a treatment or prophylactic.

In an exemplary embodiment, a method of using a composition on a subject having or suspected of having a viral respiratory infection involves administering a composition to the subject, the composition including dutasteride, wherein the composition is use as a treatment of the viral respiratory infection, a therapy for the viral respiratory infection, a prophylactic for the viral respiratory infection, a preventive measure for contracting the viral respiratory infection, a diagnosis of a type of viral respiratory infection, a prediction for respiratory disease severity of the viral respiratory infection, a prediction for determining an effective treatment or prophylactic composition, and/or a prediction for determining an effective administration dosage of the composition for use as a treatment or prophylactic.

In some embodiments, the composition is administered orally.

In some embodiments, the composition is administered so that the dutasteride is present in a range from 0.1 mg/day to 1.0 mg/day.

In some embodiments, the method involves administering the composition at any time before the subject is exposed to the viral respiratory infection.

In some embodiments, the composition is administered at any time within a time frame of thirty days prior to the patient being exposed to the viral respiratory infection.

In an exemplary embodiment, a method of using a composition on a subject having or suspected of having a viral respiratory infection involves: administering, via inhalation or injection, a small-interfering RNA (siRNA) directed against any one or combination of an androgen receptor (AR), TMPRSS2, and ACE2; wherein the viral respiratory infection includes any one or combination of coronavirus, influenza, influenza A, influenza B, SARS-CoV-1, SARS-CoV-2, MERS-CoV, or rhinoviruses.

In an exemplary embodiment, a composition for treatment of a viral respiratory infection includes any one or combination of: an androgen receptor antagonists or anti-androgen; an androgen synthesis inhibitor; an agent that counters the effect of androgens; a globulin (SHBG) stimulator; an antigonadotropin; a mineralocorticoid to suppress androgen production in the adrenal gland; a glucocorticoid to suppress androgen production in the adrenal gland; an insulin sensitizing medication; and a vaccine or an immunogen against androstenedione that reduces the level of testosterone or increases estrogen.

In some embodiments, the anti-androgen is any one or combination of: cyproterone acetate, megestrol acetate, chlormadinone acetate, spironolactone, medrogestone, oxendolone, osaterone, bifluranol acetate, finasteride, dutastride, flutamide, bicalutamide, nilutamide, topilutamide, enzalutamide, apalutamide, dienogest, drospirenone, medrogestone, nomegestrol acetate, promegestone, trimegestone, ketoconazole, abiraterone acetate, seviteronel, aminoglutethimide, episteride, alfaestradiol, isotretinoin, saw palmetto, marijuana, cannabinoids, darolutamide, EZN-4176, AZD-3514, and AZD-5312, apatorsen, galeterone, ODM-2014, TRC-253, BMS-641988, proxalutamid, Luteinizing hormone-releasing hormone (LH-RH), follicle-stimulating hormone (FSH), triptorelin pamoate, docetaxel, diethylstilbestrol, tadalafil, silodosin, tamsulosin hydrochloride, naftopidil, solifenacin succinate, tamsulosin, tamsulosin hydrochloride, alfuzosin hydrochloride, prazosin hydrochloride, doxazosin, doxazosin mesylate, solifenacin succinate, allylestrenol, benzydamine hydrochloride, cefatrizine, chlormadinone acetate, flavoxate hydrochloride, gestonorone caproate, indoramin hydrochloride, mepartricin, oxybutynin chloride, phenoxybenzamine hydrochloride, terazosin, terazosin hydrochloride, or degarelix. The agent that counters the effect of androgens is a sex hormone-binding globulin (SHBG) stimulator. The glucocorticoid is anticorticotropin. The insulin sensitizing medication is metformin.

In some embodiments, the composition is formulated to facilitate administration of the composition topically to the skin, nasally, sub-lingually orally, by injection, via inhalation, or ocular application.

In some embodiments the viral respiratory infection is any one or combination of coronavirus, influenza, influenza A, influenza B, SARS-CoV-1, SARS-CoV-2, MERS-CoV, or rhinoviruses.

In some embodiments the anti-androgen is combined with any one or combination of an anti-inflammatory agent, an anti-bacterial agent, or aspartame.

In some embodiments the composition is formulated for use as a treatment of the viral respiratory infection, a therapy for the viral respiratory infection, a prophylactic for the viral respiratory infection, and/or a preventive measure for contracting the viral respiratory infection.

In some embodiments the composition is further formulated for use as a treatment for prostate cancer, castration-resistant prostate cancer, metastatic castration-sensitive prostate cancer, non-metastatic castration-resistant prostate cancer and/or benign prostatic hyperplasia.

In an exemplary embodiment, a method of treating a patient having or suspected of having a viral respiratory infection involves administering a composition to the patient, the composition including any one or combination of: an androgen receptor antagonists or anti-androgen; an androgen synthesis inhibitor; an agent that counters the effect of androgens; a globulin (SHBG) stimulator; an antigonadotropin; a mineralocorticoid to suppress androgen production in the adrenal gland; a glucocorticoid to suppress androgen production in the adrenal gland; an insulin sensitizing medication; and vaccine or an immunogen against androstenedione that reduces the level of testosterone or increases estrogen.

In some embodiments, the anti-androgen is any one or combination of: cyproterone acetate, megestrol acetate, chlormadinone acetate, spironolactone, medrogestone, oxendolone, osaterone, bifluranol acetate, finasteride, dutastride, flutamide, bicalutamide, nilutamide, topilutamide, enzalutamide, apalutamide, dienogest, drospirenone, medrogestone, nomegestrol acetate, promegestone, trimegestone, ketoconazole, abiraterone acetate, seviteronel, aminoglutethimide, episteride, alfaestradiol, isotretinoin, saw palmetto, marijuana, cannabinoids, darolutamide, EZN-4176, AZD-3514, and AZD-5312, apatorsen, galeterone, ODM-2014, TRC-253, BMS-641988, proxalutamid, Luteinizing hormone-releasing hormone (LH-RH), follicle-stimulating hormone (FSH), triptorelin pamoate, docetaxel, diethylstilbestrol, tadalafil, silodosin, tamsulosin hydrochloride, naftopidil, solifenacin succinate, tamsulosin, tamsulosin hydrochloride, alfuzosin hydrochloride, prazosin hydrochloride, doxazosin, doxazosin mesylate, solifenacin succinate, allylestrenol, benzydamine hydrochloride, cefatrizine, chlormadinone acetate, flavoxate hydrochloride, gestonorone caproate, indoramin hydrochloride, mepartricin, oxybutynin chloride, phenoxybenzamine hydrochloride, terazosin, terazosin hydrochloride, or degarelix. The agent that counters the effect of androgens is a sex hormone-binding globulin (SHBG) stimulator. The glucocorticoid is anticorticotropin. The insulin sensitizing medication is metformin.

In some embodiments, the administration of the composition involves any one or combination of topical application to the skin, nasal application, sub-lingual application, oral application, via injection, via inhalation, or ocular application.

In some embodiments, the viral respiratory infection is any one or combination of coronavirus, influenza, influenza A, influenza B, SARS-CoV-1, SARS-CoV-2, MERS-CoV or rhinoviruses.

In some embodiments, the composition is used as a treatment for the viral respiratory infection, a therapy for the viral respiratory infection, a prophylactic for the viral respiratory infection, and/or a preventive measure for contracting the viral respiratory infection.

In some embodiments, the treatment involves administering the composition as a treatment for the viral respiratory infection and/or a prophylactic for the viral respiratory infection before, during, and/or after the patient is first diagnosed with the viral respiratory infection and/or before, during, and/or after the patient is hospitalized due to the viral respiratory infection.

In some embodiments, the composition is further used as a treatment for prostate cancer, castration-resistant prostate cancer, metastatic castration-sensitive prostate cancer, non-metastatic castration-resistant prostate cancer and/or benign prostatic hyperplasia.

In some embodiments, the method further involves predicting anti-androgen treatment response via evaluation of genetic variation in the gene and/or promotor region of the androgen receptor (AR).

In some embodiments, the method further involves guiding selection of anti-androgen treatment and/or dosage selection of the selected anti-androgen treatment based on the predicted anti-androgen treatment response.

In some embodiments, predicting the anti-androgen treatment response involves measuring polymorphisms in the AR gene.

In some embodiments, the number of cytosine-adenine-guanine (CAG) repeats in the first exon of the AR gene, the number of guanine-guanine-(any nucleotide) (GGN) repeats in the first exon in the AR gene, and/or a ratio of CAG/GGN repeats is used as the genetic variant. A cut off value for the number of CAG repeats the first exon of AR gene is used to define a person with androgen sensitivity.

In some embodiments, the cut-off value for the number of CAG repeats the first exon of AR gene is between 10 and 30.

In some embodiments, variants in the promoter region of the AR are used as the genetic variant.

In some embodiments, the anti-androgen is combined with any one or combination of an anti-inflammatory agent, an anti-bacterial agent, or aspartame.

In some embodiments, the viral respiratory infection is SARS-CoV-2.

In some embodiments, administering the composition involves administering topical skin application of finasteride at 1-30% (w/w), oral finasteride at 0.01-30 mg, dutasteride at 0.1 mg/day to 3.0 mg/day, degarelix at 24 mg-720 mg, oral cannabidiol at 1-30/mg/Kg/day, oral flutamide at 75-2,250 mg/day, enzalutamide at 16-480 mg qd, oral dutasteride at 0.025-0.75 mg/day, apalutamide at 6-180 mg 4 times per day, injection of 30-900 mg of cyproterone acetate, subcutaneous injection of 12-360 mg of degarelix, bicalutamide at 5-150 mg per day, subcutaneous injection of 12-360 mg of degarelix, oral darolutamide at 30-900 mg twice daily, abiraterone at 50-1500 mg twice daily, oral nilutamide at 30-900 mg once daily, or docetaxel at 7.5-225 mg/m2 IV over 1 hour.

In some embodiments, administering the composition involves administering topical skin application of finasteride at 1-10% (w/w), oral finasteride at 0.1-10 mg, dutasteride at 0.1 mg/day to 1.0 mg/day, degarelix at 24 mg-240 mg, oral cannabidiol at 1-10/mg/Kg/day, oral flutamide at 75-750 mg/day, enzalutamide at 16-160 mg qd, oral dutasteride at 0.025-0.25 mg/day, apalutamide at 6-60 mg 4 times per day, injection of 30-300 mg of cyproterone acetate, subcutaneous injection of 12-120 mg of degarelix, bicalutamide at 5-50 mg per day, subcutaneous injection of 12-120 mg of degarelix, oral darolutamide at 30-300 mg twice daily, abiraterone at 50-500 mg twice daily, oral nilutamide at 30-300 mg once daily, or docetaxel at 7.5-750 mg/m2 IV over 1 hour.

In an exemplary embodiment, a method of treating a patient having or suspected of having a viral respiratory infection involves: determining the risk of severity or mortality of the viral respiratory infection for the patient by identifying and measuring genetic variation in the gene and/or promotor region of any one or combination of the androgen receptor (AR), TMPRSS2, furin, or ACE2; selecting a composition and a dosage for the composition based on the determined risk of severity or mortality; and administering the composition to the patient, the composition including any one or combination of: an androgen receptor antagonists or anti-androgen; an androgen synthesis inhibitor; an agent that counters the effect of androgens; a globulin (SHBG) stimulator; an antigonadotropin; a mineralocorticoid to suppress androgen production in the adrenal gland; a glucocorticoid to suppress androgen production in the adrenal gland; an insulin sensitizing medication; and vaccine or an immunogen against androstenedione that reduces the level of testosterone or increases estrogen.

In some embodiments, the method involves use of a kit, wherein: a genetic sample via buccal swab, saliva sample, blood sample, tissue sample, and/or hair sample is obtained via a deoxyribonucleic acid (DNA) sample collection unit; polymorphisms in the androgen receptor gene are identified via a viral respiratory infection sensitivity unit; and an assay analysis is performed using a DNA diagnostic assay.

In some embodiments, the method further involves predicting anti-androgen treatment response via evaluation of a genetic variation in the gene and/or promotor region in any one or combination of AR, TMPRSS2, furin, or ACE2.

In some embodiments, the genetic variation includes any one or combination of: F877L/T878A, F877L, T878A, rs137852591, rs104894742, rs1057518177, rs1057521121, rs1057521122, rs1057523747, rs1064793480, rs1064793645, rs1064794065, rs1064794069, rs1064795250, rs1085307685, rs1085307962, rs12014709, rs1204038, rs1337080, rs137852562, rs137852563, rs137852564, rs137852565, rs137852566, rs137852567, rs137852568, rs137852569, rs137852570, rs137852571, rs137852572, rs137852573, rs137852574, rs137852575, rs137852576, rs137852577, rs137852578, rs137852579, rs137852580, rs137852581, rs137852582, rs137852583, rs137852584, rs137852585, rs137852586, rs137852587, rs137852588, rs137852589, rs137852590, rs137852592, rs137852593, rs137852594, rs137852595, rs137852596, rs137852597, rs137852598, rs137852599, rs137852600, rs137852601, rs1800053, rs201934623, rs2361634, rs5031002, rs5918757, rs6152, rs6624304, rs750324117, rs754201976, rs755226547, rs759327087, rs864622007, rs869320731, rs869320732, rs878853033, rs886039558, rs886041050, rs886041128, rs886041129, rs886041130, rs886041131, rs886041132, rs886041133, rs886041352, rs9332969, or rs9332971; one or more of: rs12329760, rs2070788, rs383510, rs463727, rs34624090, rs55964536, rs734056, rs4290734, rs34783969, rs11702475, rs35899679, rs35041537, rs8134378, rs2070788, rs9974589, rs7364083, or rs2070788; one or more of: rs2285666, G8790A, rs35803318, rs1978124, rs2048683, rs2074192, rs2106809, rs2285666, rs233575, rs4240157, rs4646155, rs4646156, rs4646174, rs4646176, rs4646188, rs6632677, rs714205, or rs879922; or one or more of: rs17514846, rs2071410, rs4702, rs4932178, rs6226, or rs6227.

DETAILED DESCRIPTION

SARS-CoV-2 is part of the coronavirus family of viruses including SARS-CoV-1 and MERS-CoV. Coronavirus predominantly infects type II pneumocytes in the human lung (See Shieh W J, Hsiao C H, Paddock C D, Guarner J, Goldsmith C S, et al. Immunohistochemical, in situ hybridization, and ultrastructural localization of SARS-associated coronavirus in lung of a fatal case of severe acute respiratory syndrome in Taiwan. Hum Pathol. 2005; 36(3): 303-309). It has been demonstrated that SARS-CoV-2 cell entry depends on priming of a viral spike surface protein by transmembrane protease serine 2 (TMPRSS2) present in the host. In type II pneumocytes, TMPRSS2 expression is associated with an increase in androgen receptor (AR) expression (See Mikkonen L, Pihlajamaa P, Sahu B, Zhang F P, Jänne O A. Androgen Receptor and Androgen-Dependent Gene Expression in Lung. Mol Cell Endocrinol. 2010; 317 (1-2): 14-24), specifically connecting AR expression to SARSCoV-2, due to AR-regulated TMPRSS2 gene promoter (See Lin B, Ferguson C, White J T, Wang S, Vessella R, True L D, et al. Prostate-localized and androgen-regulated expression of the membrane-bound serine protease TMPRSS2. Cancer Res 1999; 59: 4180-4). Moreover, angiotensin converting enzyme 2 (ACE2) has been recognized as the attachment molecule to the viral spike surface protein, thus termed the "receptor of SARS-CoV-2" (See Y. Qiu, Y.-B. Zhao, Q. Wang, J.-Y. Li, Z.-J. Zhou, C.-H. Liao, X.-Y. Ge, Predicting the angiotensin converting enzyme 2 (ACE2) utilizing capability as the receptor of SARS-CoV-2, Microbes and Infection, https://doi.org/10.1016/j.micinf.2020.03.003).

As used herein, the terms "prevent" or "prevention" and other derivatives of the words, when used in reference to viral respiratory infection, e.g., viral respiratory infection, refer to a reduced likelihood of viral respiratory infection in an individual receiving a given treatment relative to that of a similar individual at risk for viral respiratory infection but not receiving that treatment. As such, the terms "prevent"

and "prevention" encompass a treatment that results in a lesser degree of viral respiratory infection, e.g., viral respiratory infection, than would be otherwise expected for a given individual. Efficacy for prevention of viral respiratory infection, e.g., viral respiratory infection, can be established through controlled studies, e.g., in which a subject is administered a treatment (e.g., an inhaled treatment) and another subject is administered a placebo. Under these circumstances, if the subject treated with the inhaled treatment undergoes less severe viral respiratory infection symptoms over time relative to the subject receiving the placebo, e.g., at least 5% less, at least 10% less, at least 15% less, at least 20% less, at least 25% less, at least 30% less, at least 35% less, at least 40% less, at least 45% less, at least 50% less or beyond, the treatment is effective for the prevention of viral respiratory infection As used herein, the terms "treat," "treatment," or "treating" refer to therapeutic treatments, wherein the object is to reverse, alleviate, ameliorate, inhibit, slow down or stop the progression or severity of a disease or condition, e.g., viral respiratory infection. The term "treating" includes reducing or alleviating at least one adverse effect or symptom of a disease or condition, e.g., viral respiratory infection. Treatment is generally "effective" if one or more symptoms are reduced. Alternatively, treatment is "effective" if the progression of a disease is reduced or halted. That is, "treatment" includes not just the improvement of symptoms, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if: 1) the risk or propensity of a person having a viral respiratory infection being hospitalized, being admitted to an intensive care unit (ICU), or dying as a result is reduced; 2) the rate at which a person having a viral respiratory infection recovers or stabilizes is increased; 3) the rate at which a person having a viral respiratory infection is discharged from the hospital is increased; 4) the ability for a person having a viral respiratory infection to recover or stabilize is improved; 5) the ability to diagnose a person as having a viral respiratory infection is improved; 6) the time to diagnose a person having a viral respiratory infection is reduced; 7) the ability to prevent a person from being infected with a viral respiratory infection is improved; 8) the ability to predict viral respiratory disease severity (e.g., is a ventilator or respirator will be needed for treatment) is increased. The term "treatment" of a disease also includes providing relief from the symptoms or side-effects of the disease (including palliative treatment). Treatment can involve administering a therapeutically effective amount of any one or combination of the compositions disclosed herein.

As used herein the term "comprising" or "comprises" is used in reference to compositions, methods, etc. refers to component(s) or method steps that are present in the method or composition, yet allows for the composition, method, etc. to also include unspecified elements.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used herein the term "viral respiratory infection" refers to all forms of human lung disease stemming from a viral infection including coronavirus, influenza, influenza A, influenza B, SARS-CoV-1, SARS-CoV-2, MERS-CoV and rhinoviruses. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Various aspects of the technology describe detecting androgen sensitivity in a subject by measuring polymorphisms in the androgen receptor gene. Androgen Receptor (AR) genetic variation refers to DNA genetic variations, expression of AR in specific tissue (RNA), including methylation analysis of AR (i.e., in the case of X-chromosome inactivation). Specific details for detecting polymorphisms in the androgen receptor can be found in literature, e.g., See Androgens and Androgen Receptor: Mechanisms, Functions, and Clini Applications. United States, Springer U S, 2012, which is incorporated here in its entirety. Polymorphisms in the androgen receptor can be used to infer a subject has androgen sensitivity.

Applicants disclose herein systems, methods, and kits for treating, preventing, and diagnosing viral respiratory infection by first measuring polymorphisms in the androgen receptor gene. The method includes the use of compositions including any one or combination of the following: androgen receptor antagonists, androgen synthesis inhibitors, agents that counter the effect of androgens such as sex hormone-binding globulin (SHBG) stimulators, antigonadotropins, mineralocorticoids and glucocorticoids (anticorticotropins) suppressing androgen production in the adrenal gland, insulin sensitizing medications (e.g., metformin), and vaccines or immunogens against androstenedione that reduce the level of testosterone as a treatment for viral respiratory disease. The use of the composition can involve administering the composition to a subject or a patient. For instance, the composition can be administered topically, nasally, orally, by injection, or be applied topically to the lung, i.e. inhaled. Compositions applied to a subject alter androgen receptor function and subsequently down stream genes under regulatory control of the androgen receptor. Such genes include but are not limited to, angiotensin converting enzyme 2 (ACE2), furin, and transmembrane protease serine 2 (TMPRSS2). Blocking the production of certain proteins in the lung may be beneficial to altering viral entry into cells or bolstering host immunity. For example, TMPRSS2 priming of a viral spike surface protein is required for SARS-CoV-2 cell entry; TMPRSS2 expression is under control of the androgen receptor. As such, blocking the expression of the androgen receptor or altering AR activity (e.g., with and AR antagonist) would decrease the amount of TMPRSS2 expression and lead to reduced viral entry. Other embodiments are described below.

In certain embodiments, a genetic variation in the androgen receptor (AR) gene can be used to predict mortality from viral respiratory infection. In another embodiment, a genetic variation in the androgen receptor (AR) gene can be used to predict viral respiratory infection symptom severity. In yet another embodiment, a genetic variation in the androgen receptor (AR) gene can be used to predict if a patient with viral respiratory infection will need a ventilator or a respirator.

In certain embodiments, a genetic variation in the androgen receptor (AR) gene can be used to predict COVID-19 mortality. In another embodiment, a genetic variation in the androgen receptor (AR) gene can be used to predict COVID-19 symptom severity. In yet another embodiment, a genetic variation in the androgen receptor (AR) gene can be used to predict COVID-19 patient's need for a ventilator or a respirator.

Many genetic variations in the androgen receptor (AR) gene can be used to predict viral respiratory disease severity but may include, the number cytosine-adenine-guanine (CAG) repeats in the first exon of AR gene. In certain embodiments of present invention, a cut off value for the number of CAG repeats the first exon of AR gene can be used to define a person with androgen sensitivity. In one embodiment, the cut-off value for the number of CAG repeats the first exon of AR gene is 24.

Various aspects of the technology describe detecting androgen sensitivity in a subject by measuring polymorphisms in the androgen receptor gene. Androgen Receptor (AR) genetic variation refers to DNA genetic variations, expression of AR in specific tissue (RNA), including methylation analysis of AR (i.e., in the case of X-chromosome inactivation). Androgen sensitivity may also include DNA genetic variations in androgen response elements (ARE) of genes under the regulatory control of the AR. Examples of genes containing AREs include, but are not limited to, TMPRSS2 and ACE2. Polymorphisms in the androgen response elements can also be used to infer a subject has androgen sensitivity.

In certain embodiments of the present invention genetic variations in the androgen receptor (AR) gene or the promoter region of the AR can be used to predict a treatment response. In another embodiment of the present invention genetic variations in the androgen receptor (AR) gene or the promoter region of the AR can be used to select a dosage of a treatment drug. In certain embodiments genetic variations in the androgen receptor (AR) gene or the promoter region of the AR are single nucleotide polymorphisms (SNPs). In other embodiments SNPs that are associated with AR expression or function are used.

Examples of genetic variations in the androgen receptor (AR) gene or the promoter region of the AR, or are associated with AR expression or function include but are not limited to F877L/T878A, F877L, T878A, rs137852591, rs104894742, rs1057518177, rs1057521121, rs1057521122, rs1057523747, rs1064793480, rs1064793645, rs1064794065, rs1064794069, rs1064795250, rs1085307685, rs1085307962, rs12014709, rs1204038, rs1337080, rs137852562, rs137852563, rs137852564, rs137852565, rs137852566, rs137852567, rs137852568, rs137852569, rs137852570, rs137852571, rs137852572, rs137852573, rs137852574, rs137852575, rs137852576, rs137852577, rs137852578, rs137852579, rs137852580, rs137852581, rs137852582, rs137852583, rs137852584, rs137852585, rs137852586, rs137852587, rs137852588, rs137852589, rs137852590, rs137852592, rs137852593, rs137852594, rs137852595, rs137852596, rs137852597, rs137852598, rs137852599, rs137852600, rs137852601, rs1800053, rs201934623, rs2361634, rs5031002, rs5918757, rs6152, rs6624304, rs750324117, rs754201976, rs755226547, rs759327087, rs864622007, rs869320731, rs869320732, rs878853033, rs886039558, rs886041050, rs886041128, rs886041129, rs886041130, rs886041131, rs886041132, rs886041133, rs886041352, rs9332969, or rs9332971.

In certain embodiments of the present invention genetic variations in the androgen response elements (ARE) of genes under the regulatory control of the AR can be used to predict a treatment response. In another embodiment of the present invention genetic variations in the androgen response elements (ARE) of genes under the regulatory control of the AR can be used to select a dosage of a treatment drug. In certain embodiments genetic variations in the androgen response elements (ARE) of genes under the regulatory control of the AR are single nucleotide polymorphisms (SNPs). In some embodiments of the present invention genetic variations in AREs in the TMPRSS2, ACE2, and furin gene are used. In other embodiments SNPs in the AREs or coding regions of TMPRSS2, ACE2, and furin gene are used. In other embodiments SNPs that are associated with TMPRSS2, ACE2, and furin expression or function are used.

Examples of genetic variations in the AREs, promoter region, coding region, or that are associated with TMPRSS2 expression or function include but are not limited to rs12329760, rs2070788, rs383510, rs463727, rs34624090, rs55964536, rs734056, rs4290734, rs34783969, rs11702475, rs35899679, rs35041537, rs8134378, rs2070788, rs9974589, rs7364083, and rs2070788.

Examples of genetic variations in the AREs, promoter region, coding region, or that are associated with ACE2 expression or function include but are not limited to rs2285666, G8790A, rs35803318, rs1978124, rs2048683, rs2074192, rs2106809, rs2285666, rs233575, rs4240157, rs4646155, rs4646156, rs4646174, rs4646176, rs4646188, rs6632677, rs714205, and rs879922.

Examples of genetic variations in the furin, promoter region, coding region, or that are associated with furin expression or function include but are not limited to rs17514846, rs2071410, rs4702, rs4932178, rs6226, and rs6227.

Androgen sensitivity may also include DNA genetic variations in androgen response elements (ARE) of genes under the regulatory control of the AR. Examples of genes containing AREs include, but are not limited to, TMPRSS2, furin and ACE2.

In yet another embodiment of the present invention, genetic variations in the TMPRSS2, furin or ACE2 gene or the promoter region of the TMPRSS2, furin or ACE2 can be used to predict a treatment response. In another embodiment of the present invention genetic variations in the TMPRSS2, furin or ACE2 gene or the promoter region of the TMPRSS2, furin or ACE2 can be used to select a dosage of a treatment drug.

In certain embodiments, a genetic variation in the TMPRSS2, furin or ACE2 gene can be used to predict mortality from viral respiratory infection. In another embodiment, a genetic variation in the TMPRSS2, furin or ACE2 gene can be used to predict viral respiratory infection symptom severity. In yet another embodiment, a genetic variation in the TMPRSS2, furin or ACE2 gene can be used to predict if a patient with viral respiratory infection will need a ventilator or a respirator.

In certain embodiments, a genetic variation in a genetic variation in the TMPRSS2, furin or ACE2 gene can be used to predict COVID-19 mortality. In another embodiment, a genetic variation in a genetic variation in the TMPRSS2, furin or ACE2 gene can be used to predict COVID-19 symptom severity. In yet another embodiment, a genetic variation in a genetic variation in the TMPRSS2, furin or ACE2 gene can be used to predict COVID-19 patient's need for a ventilator or a respirator.

Many genetic variations in the androgen receptor (AR) gene can be used to predict viral respiratory disease severity but may include, the number of CAG repeats in the first exon of AR gene. In certain embodiments of present invention a cut off value for the number of CAG repeats the first exon of AR gene can be used to define a person with androgen sensitivity. In one embodiment the cut-off value for the number of CAG repeats the first exon of AR gene is 24. In another embodiment, the number guanine-guanine-(any nucleotide) (GGN) (polyglycine) repeats in the first exon of AR gene. In certain embodiments of present invention the number of GGN repeats is between 10 and 30. In another embodiment, the number of GGN repeats can be used to define a person with androgen sensitivity. In one embodiment the ratio of CAG to GGN repeats the first exon of AR gene is used to define a person with androgen sensitivity. In some embodiments the number of CAG, GGN, or the ratio of CAG/GGN is used to predict a treatment response or choose a dosage of a drug or treatment regimen.

In certain embodiments, a genetic variation in the TMPRSS2, furin or ACE2 gene is used as a predictor of anti-androgen treatment response for viral respiratory infection. In certain embodiments, a genetic variation in the TMPRSS2, furin or ACE2 gene is used to guide selection of the appropriate anti-androgen treatment for viral respiratory infection. In certain embodiments, a genetic variation in the TMPRSS2, furin or ACE2 gene is used as a predictor of anti-androgen treatment response for COVID-19. In certain embodiments, a genetic variation in the TMPRSS2, furin or ACE2 gene is used to guide selection of the appropriate anti-androgen treatment for COVID-19. In certain embodiments, a genetic variation in the TMPRSS2, furin or ACE2 gene is used to guide dosage selection of the appropriate anti-androgen treatment for COVID-19.

In certain embodiments, a genetic variation in the AR gene and either the TMPRSS2, furin or ACE2 gene is used as a predictor of anti-androgen treatment response for viral respiratory infection. In certain embodiments, a genetic variation in the AR gene and either the TMPRSS2, furin or ACE2 gene is used to guide selection of the appropriate anti-androgen treatment for viral respiratory infection. In certain embodiments, a genetic variation in the AR gene and either the TMPRSS2, furin or ACE2 gene is used as a predictor of anti-androgen treatment response for COVID-19. In certain embodiments, a genetic variation in the AR gene and either the TMPRSS2, furin or ACE2 gene is used to guide selection of the appropriate anti-androgen treatment for COVID-19. In certain embodiments, a genetic variation in the AR gene and either the TMPRSS2, furin or ACE2 gene is used to guide dosage selection of the appropriate anti-androgen treatment for COVID-19.

In certain embodiments of the present invention, a kit containing a DNA sample collection tool is envisioned. The genetic sample can be obtained by buccal swab, saliva, blood, or tissue samples. The genetic sample can also be obtained from a plucked hair sample. For example, a kit is disclosed for detecting COVID-19 androgen sensitivity; the kit is an in-vitro diagnostic medical device intended to identify polymorphisms in the androgen receptor gene. The kit includes a collection device (buccal swab) and a DNA diagnostic assay (laboratory based). DNA samples are collected from a patient and mailed to a laboratory for processing.

In certain embodiments, the number of CAG repeats in the first exon of the AR gene is used as a genetic variant. In other embodiments, the variants in the promoter region of the AR are used as a genetic variant. In another embodiment, a shorter CAG repeat (compared to normal) may predispose patients to more severe viral respiratory infections. In another embodiment, a shorter CAG repeat (compared to normal) may predispose patients to more severe infection fro COVID-19. In another embodiment, the length of the CAG repeat determines anti-androgen dosing for the treatment of viral respiratory infections.

In certain embodiments, a method of treatment of COVID-19 patient involves administering an anti-androgen to a COVID-19 patient where there anti-androgen is any one or combination of: cyproterone acetate, megestrol acetate, chlormadinone acetate, spironolactone, medrogestone, oxendolone, osaterone, bifluranol acetate, finasteride, dutastride, flutamide, bicalutamide, nilutamide, topilutamide, enzalutamide, apalutamide, dienogest, drospirenone, medrogestone, nomegestrol acetate, promegestone, trimegestone, ketoconazole, abiraterone acetate, seviteronel, aminoglutethimide, episteride, alfaestradiol, isotretinoin, saw palmetto, marijuana, cannabinoids, darolutamide, EZN-4176, AZD-3514, and AZD-5312, apatorsen, galeterone, ODM-2014, TRC-253, BMS-641988, proxalutamid, Luteinizing hormone-releasing hormone (LH-RH), follicle-stimulating hormone (FSH), triptorelin pamoate, docetaxel, diethylstilbestrol, tadalafil, silodosin, tamsulosin hydrochloride, naftopidil, solifenacin succinate, tamsulosin, tamsulosin hydrochloride, alfuzosin hydrochloride, prazosin hydrochloride, doxazosin, doxazosin mesylate, solifenacin succinate, allylestrenol, benzydamine hydrochloride, cefatrizine, chlormadinone acetate, flavoxate hydrochloride, gestonorone caproate, indoramin hydrochloride, mepartricin, oxybutynin chloride, phenoxybenzamine hydrochloride, terazosin, terazosin hydrochloride, or degarelix. As explained herein, the method of treatment can involve administration of a composition that includes an anti-androgen as an ingredient of the composition. The anti-androgen can be present in percent amounts ranging from 0% to 100%.

In certain embodiments, a method of treatment of COVID-19 patient involves administering an agent that counters the effect of androgens such as sex hormone-binding globulin (SHBG) stimulators. As explained herein, the method of treatment can involve administration of a composition that includes said agent as an ingredient of the composition. The agent can be present in percent amounts ranging from 0% to 100%.

In certain embodiments, a method of treatment of COVID-19 patient involves administering an antigonadotropin. As explained herein, the method of treatment can involve administration of a composition that includes an antigonadotropin as an ingredient of the composition. The antigonadotropin can be present in percent amounts ranging from 0% to 100%. The word antigonadotropin includes Gonadotropin-releasing hormone antagonists (GnRH antagonists). Some GnRH antagonist are: Elagolix, Cetrorelix, Relugolix, Degarelix In certain embodiments, a method of treatment of COVID-19 patient involves administering a mineralocorticoid and/or a glucocorticoid (e.g., anticorticotropin) suppressing androgen production in the adrenal gland. As explained herein, the method of treatment can involve administration of a composition that includes a mineralocorticoid and/or a glucocorticoid as an ingredient of the composition. The mineralocorticoid and/or a glucocorticoid can be present in percent amounts ranging from 0% to 100%.

In certain embodiments, a method of treatment of COVID-19 patient involves administering an insulin sensitizing medication (e.g., metformin). As explained herein, the method of treatment can involve administration of a composition that includes an insulin sensitizing medication as an ingredient of the composition. The insulin sensitizing medication can be present in percent amounts ranging from 0% to 100%.

In certain embodiments, a method of treatment of COVID-19 patient involves administering a vaccine or immunogen against androstenedione that reduces the level of testosterone or increases estrogen. Examples of such vaccines and immunogens can be ovandrotone albumin and androstenedione albumin. As explained herein, the method of treatment can involve administration of a composition that includes said vaccine or immunogen as an ingredient of the composition. The vaccine or immunogen can be present in percent amounts ranging from 0% to 100%.

RNA interference (RNAi) is a biological process in which RNA molecules inhibit gene expression or translation, by neutralizing targeted mRNA molecules. RNAi selectively knocks down target genes. RNAi can also mean other names, including co-suppression, post-transcriptional gene silencing (PTGS), siRNA, quelling, or gene knock-down. In one embodiment of the present invention RNAi is used to knock down the AR. In one embodiment of the present invention RNAi is used to knock down the AR in type II pneumocytes. In one embodiment of the present invention RNAi is used to knock down the TMPRSS2. In one embodiment of the present invention RNAi is used to knock down the TMPRSS2 in type II pneumocytes. In another embodiment, RNAi is used to knock down ACE2. In one embodiment the RNAI treatment is inhaled in another embodiment the RNAi treatment is administered (e.g., via injection). In one embodiment the RNAI treatment is used to treat upper respiratory disease or any viral infection disclosed herein (e.g., coronavirus, influenza, influenza A, influenza B, SARS-CoV-1, SARS-CoV-2, MERS-CoV and rhinoviruses). In one embodiment, a small-interfering RNA (siRNA) directed against androgen receptor (AR) is administered. In one embodiment, a small-interfering RNA (siRNA) directed against TMPRSS2 is administered. In one embodiment, a small-interfering RNA (siRNA) directed against ACE2 is administered. Upon administration of anti-AR siRNA, for example, SXL01, the siRNAs bind to AR mRNAs, which may result in the inhibition of translation of the AR protein and by preventing AR expression, AR-mediated signaling is decreased, which leads to inhibition of TMPRSS2 or ACE2. In one embodiment, anti-AR siRNA, for example, SXL01, is administered (e.g., inhaled) to treat any viral infection disclosed herein (e.g., coronavirus, influenza, influenza A, influenza B, SARS-CoV-1, SARS-CoV-2, MERS-CoV and rhinoviruses). In one embodiment, anti-AR siRNA, for example, SXL01, is inhaled to treat SARS-CoV-2.

In certain embodiments, use of an anti-androgen for treatment can mean a treatment that promotes the production of estrogen. In another embodiment use of estrogen is the treatment. Examples of drugs that promote the production of estrogen include, but are not limited to, estrogen, estradiol, Premarin (conjugated estrogens), medroxyprogesterone acetate, Provera, medroxyprogesterone, Vivelle-Dot (estradiol patch).

In certain embodiments, use of degarelix can be used as the treatment and/or prophylactic. For instance, degarelix can be administered for a predetermined period of time (e.g., 1 week, 2, weeks, 1 month, 2 months, etc.). The administration of degarelix can be in single or multiple doses per day over the predetermined time period. For instance, the administration of degarelix can involve a 240 mg dose comprising a first injection of 120 mg and a second injection of 120 mg every 24 hours. This first and second injection routine can be administered for 1 month. The administration of degarelix can be for treatment and/or prophylactic use before, during, and/or after a patient is first diagnosed with the viral respiratory infection and/or before, during, and/or after a patient is hospitalized due to the viral respiratory infection.

In certain embodiments, an anti-androgen is used as a prophylactic treatment for viral respiratory infection.

In certain embodiments, an anti-androgen is prescribed to a patient believed to be infected with COVID-19 as a prophylactic for viral respiratory infection, i.e. severe COVID disease. In another embodiment an anti-androgen is prescribed to a patient to prevent COVID disease symptoms from developing. In certain embodiments, apalutamide is prescribed to patients who are diagnosed with COVID-19 infection but have yet to demonstrate symptoms. It is specifically envisioned that hospitalization rates of populations given an anti-androgen or a placebo at early diagnosis COVID-19 can be used as a clinical endpoint for determining the efficacy of an anti-androgen for preventing the progression of COVID-19 disease. It is specifically envisioned that hospitalization rates of populations given apalutamide or a placebo at early diagnosis COVID-19 can be used as a clinical endpoint for determining the efficacy of apalutamide for preventing the progression of COVID-19 disease.

In certain embodiments, dutasteride (Bis(trifluoromethyl)phenyl]-3-oxo-4-aza-5α-androst-1-ene-17β-carboxamide) is used as treatment for COVID-19. In certain embodiments, dutasteride can be administered orally. In certain embodiments, the dutasteride is used as a prophylactic treatment for COVID-19. The treatment can involve administration of dutasteride ranging from 0.1 mg/day to 1.0 mg/day. The treatment can involve administration of dutasteride before being exposed to the viral respiratory infection. This can include administration of dutasteride at any time before being exposed to the viral respiratory infection up to and including 30 days prior to being exposed.

In certain embodiments, a genetic variation in the AR gene is used as a predictor of anti-androgen treatment response for viral respiratory infection. In certain embodiments, a genetic variation in the AR gene is used to guide selection of the appropriate anti-androgen treatment for viral respiratory infection. In certain embodiments, a genetic variation in the AR gene is used as a predictor of anti-androgen treatment response for COVID-19. In certain embodiments, a genetic variation in the AR gene is used to guide selection of the appropriate anti-androgen treatment for COVID-19. In certain embodiments, a genetic variation in the AR gene is used to guide dosage selection of the appropriate anti-androgen treatment for COVID-19.

In one embodiment of the present invention, a composition including an anti-androgen is used to treat patients with any one or combination of benign prostatic hyperplasia (BPH), prostate cancer, castration-resistant prostate cancer, metastatic castration-sensitive prostate cancer, or non-metastatic castration-resistant prostate cancer. In some embodiments, the composition including an anti-androgen can be used to treat patients with any viral infection disclosed herein (e.g., coronavirus, influenza, influenza A, influenza B, SARS-CoV-1, SARS-CoV-2, MERS-CoV and rhinoviruses) and/or any one or combination of benign prostatic hyperplasia (BPH), prostate cancer, castration-resistant prostate cancer, metastatic castration-sensitive prostate cancer, or non-metastatic castration-resistant prostate cancer.

Any of the compositions disclosed herein can include other ingredients (e.g., carrier agents) to facilitate use or administration of the composition via injection, oral administration, nasal administration, topological administration, etc. For instance, a composition can include a carrier or delivery vehicle optimized for delivery of the composition to the lung. As another example, a composition can be formulated to be released using several different formulations or release methods including time release, creams, ointments, sprays, capsules, or other release methods. Capsules or vehicles that encapsulate the composition can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam.

In certain embodiments, the uses (e.g., treatment, therapy, prophylactic treatment, prevention, diagnosis, prediction, selection of a drug, selection of a dosage, etc.) of the composition(s) disclosed herein can be administered by inhalation, oral, nasal, injection, topological application, ocular application, etc. In certain embodiments, the uses of the composition can involve being administered by nebulization or vaping. In certain embodiments, the uses can involve being administered systemically in oral, intravenous injection, subcutaneous injection. In certain embodiments, the uses can involve being administered topically.

In one embodiment of the present invention a therapy involving the use of a composition is delivered as a topical ocular solution, i.e., eye drop, spray, solution, lotion, gel, ointment.

In another embodiment of the present invention, a topically applied ocular anti-androgen solution, is used as a prophylactic treatment against any viral infection disclosed herein (e.g., coronavirus, influenza, influenza A, influenza B, SARS-CoV-1, SARS-CoV-2, MERS-CoV and rhinoviruses).

In another embodiment of the present invention, a topically applied ocular anti-androgen solution, is used as a prophylactic treatment against any viral infection disclosed herein (e.g., coronavirus, influenza, influenza A, influenza B, SARS-CoV-1, SARS-CoV-2, MERS-CoV and rhinoviruses). The anti-androgen can be applied every 1 hr, 2 hrs, 4 hrs, 8 hrs, 12 hrs, once per day, twice daily, three times a day or every other day.

In another embodiment of the present invention, a topically applied ocular anti-androgen solution, is used as a treatment against any viral infection disclosed herein (e.g., coronavirus, influenza, influenza A, influenza B, SARS-CoV-1, SARS-CoV-2, MERS-CoV and rhinoviruses).

In another embodiment of the present invention, a topically applied ocular anti-androgen solution, is used as a treatment against any viral infection disclosed herein (e.g., coronavirus, influenza, influenza A, influenza B, SARS-CoV-1, SARS-CoV-2, MERS-CoV and rhinoviruses) and benign prostatic hyperplasia and/or androgenetic alopecia.

In another embodiment of the present invention, a topically applied ocular anti-androgen solution, is used as a treatment against any viral infection disclosed herein (e.g., coronavirus, influenza, influenza A, influenza B, SARS-CoV-1, SARS-CoV-2, MERS-CoV and rhinoviruses) and hirsutism.

In another embodiment of the present invention, a topically applied ocular anti-androgen solution, is used as a treatment against any viral infection disclosed herein (e.g., coronavirus, influenza, influenza A, influenza B, SARS-CoV-1, SARS-CoV-2, MERS-CoV and rhinoviruses) and polycystic ovary syndrome.

It should be noted that any of the ingredients disclosed herein can be used in combination with other any one or combination of other ingredients (e.g., an anti-androgen can be used with an agent that counters the effect of androgens, an antigonadotropin can be used with a mineralocorticoid, an insulin sensitizing medication can be used with an anti-androgen and a mineralocorticoid, etc.). Thus, it should be understood that a reference to a composition can (to the extent it is not impossible to do so) include a single composition, a combination of compositions, and/or a combination of a composition with another ingredient.

It should also be understood that a reference to a use of a composition can (to the extent it is not impossible to do so) involve use of any one or combination of uses (e.g., treatment, therapy, prophylactic treatment, prevention, diagnosis, prediction, selection of a drug, selection of a dosage, etc.).

It should also be understood that a reference to an administration of a composition can (to the extent it is not impossible to do so) involve any one or combination of administrations (e.g., inhalation, oral, nasal, injection, topological application, ocular application, etc.).

In some embodiments, provided herein is an anti-androgen formulated with a carrier or delivery vehicle optimized for delivery of the anti-androgen treatment to the lung. An anti-androgen can be released using several different formulations or release methods including time release, creams, ointments, sprays, capsules, or other release methods. Capsules or vehicles that encapsulate the anti-androgen can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam.

In some embodiments, the anti-androgen is combined with an anti-inflammatory agent, such as an NSAID.

In some embodiments, the anti-androgen is combined with an anti-bacterial agent, such as an azithromycin.

In some embodiments, the anti-androgen is combined with aspartame.

In some embodiments, the anti-androgen treatment is administered orally.

In other embodiments, the anti-androgen treatment is administered nasally.

In other embodiments, the anti-androgen treatment is administered by inhalation.

In other embodiments, the anti-androgen treatment is administered topically via the skin.

In other embodiments, the anti-androgen treatment is administered intramuscularly or intravenously.

Any of the aforementioned anti-androgens can be used routinely, e.g., once daily, twice daily, every other day, once a week.

As noted herein, any of the compositions disclosed herein can be used as a treatment for a viral respiratory infection and/or a prophylactic for a viral respiratory infection. The viral respiratory infection can include any one or combination of coronavirus, influenza, influenza A, influenza B, SARS-CoV-1, SARS-CoV-2, MERS-CoV and rhinoviruses. Any of the compositions can be used as a treatment and/or a prophylactic before, during, and/or after a patient is first diagnosed with the viral respiratory infection and/or before, during, and/or after a patient is hospitalized due to the viral respiratory infection.

As described herein, efficacy of treatment to treat or prevent viral respiratory infection can be categorized via patient conditions related to: being discharged from the hospital, being hospitalized, being admitted to and intensive care unit (ICU), or dying as a result of the viral respiratory infection. Efficacy may also be determined by the hospitalization rates of populations given an anti-androgen or a placebo at early diagnosis of COVID-19.

The various methods and techniques described herein provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed herein, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

The recitation of ranges of values herein is merely intended to serve as a shorthand method of referring individually to each separate value falling within the range (the range including the end points of the range). Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the herein-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that can have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

EXAMPLES

Example 1

In-Vitro Diagnostic Test to Predict COVID-19 Mortality and Disease Severity

Investigational Device

Device Name: COVID-19 Androgen Sensitivity Test (CoVAST)

Device Background:

The COVID-19 Androgen Sensitivity Test is a non-invasive In-Vitro Diagnostic device that utilizes qualitative DNA genotyping. The COVID-19 Androgen Sensitivity Test requires a health care professional to collect a DNA sample using an FDA cleared DNA sample collection kit. The sample collection kit is an ORAcoilectDx OCD-100A device manufactured by DNA Genotek, Inc (previously cleared under K152464). The COVID-19 Androgen Sensitivity Test is intended to be performed at a Clinical Laboratory Improvement Amendments (CLIA) certified laboratory. The reagents used in performing the COVID-19 Androgen Sensitivity Test are manufactured in a GMP facility. COVID-19 Androgen Sensitivity Test reports the results of the DNA genotyping.

Trial Conduct

The following describes how the methods and compositions disclosed herein may be implemented.

It is contemplated for a trial study to be conducted in compliance with the protocol approved by the Institutional Review Board (IRB), and according to Good Clinical Practice standards. The CoVAST Test used in this study can be manufactured according to GMP and the specimens are analyzed at a CLIA laboratory. It is contemplated that no deviation from the protocol will be implemented without the prior review and approval of the IRB except where it may be necessary to eliminate an immediate hazard to a research subject. In such case, the deviation should reported to the IRB as soon as possible.

Population

In an exemplary implementation, the trial study can be a multi-center study. For instance, the study may be conducted in at least 2 countries—Spain and the US. It is contemplated for the protocol disclosed herein to be followed without deviation in each country. It is contemplated for there to be a minimum of 2 separate sites and 2 separate PIs (if not deviating from the protocol then there will be a minimum of 2 separate sites and 2 separate PIs). In the US, the study should be approved by an IRB and in the other countries by the appropriate Ethics Committees (if not deviating from the protocol then the study will be approved by an IRB in the US and by the appropriate Ethics Committees in other countries).

The population for this study can be subjects recruited from each site (e.g., hospital) (if not deviating from the protocol then the subjects will be recruited from each site (hospital)). Subjects can be males requesting a SARS-CoV-2 test following respiratory symptoms (if not deviating from the protocol then the subjects will be males requesting a SARS-CoV-2 test following respiratory symptoms). Subjects can be males 18 years and older of any ethnicity (if not deviating from the protocol then the subjects will be males 18 years and older of any ethnicity).

Trial Objectives

The primary purpose of the study can be to determine the predictive value of the CoVAST Test (if not deviating from the protocol then the primary purpose of the study will be to determine the predictive value of the CoVAST Test). The predictive value can be calculated based on the positive percent agreement and negative percent agreement of the CoVAST Test (if not deviating from the protocol then the predictive value will be calculated based on the positive percent agreement and negative percent agreement of the CoVAST Test). The results can be presented in 2×2 tables (if not deviating from the protocol then the results will be presented in 2×2 tables).

Trial Design

Primary Study Endpoints/Secondary Endpoints

Primary Outcome Measures:

Severity of Disease (discharged, hospitalization, admission to intensive care unit [ICU], or death) [Baseline, Day 7, Day 14, Day 21, Day 28]

Study Design/Type

The study can be (or will be) a prospective cross-sectional observational study. The study can (or will) have 2 arms:

Arm 1: Males first tested positive for SARS-CoV-2 at the site (hospital) with CAG length<24 (based on the CoVAST Test)

Arm 2: Males first tested positive for SARS-CoV-2 at the site (hospital) with CAG length>=24 (based on the CoVAST Test)

Study Environment:

This can be (or will be) a multi-center study to be conducted in at least 2 countries—Spain and the US. Again, it is contemplated for the following protocol to be followed without deviation. The protocol can (or will) be followed in each country. There can (or will) be a minimum of 2 separate sites and 2 separate PIs. In the US, the study can (or will) be approved by an IRB and in the other countries by the appropriate Ethics Committees.

The study can (or will) be conducted at the site(s) listed herein i.e., the PI's hospital. All data collection including sample collection can (or will) be performed at the site.

Study Design:

Study Phase Ia: Screening (First Site Visit)

The PI can (or will) screen each potential subject for the inclusion and exclusion criteria.

Study Phase Ib: Enrollment (First Site Visit)

Each qualified subject can (or will) complete and sign the informed consent form.

Each subject can (or will) be assigned a subject study number.

Study Phase Ic: Sample Collection (First Site Visit)

For each subject, the PI can (or will) collect the saliva DNA sample using the CoVAST Test Sample Collection Kit. The sample collection can (or will) be performed in accordance with IFU for the collection kit.

The sample collection kit can (or will) be sent to the hospital laboratory.

All information can (or will) be recorded in the appropriate CRFs.

Study Phase Id: Hospital Laboratory (First Site Visit)

The hospital laboratory can (or will) extract the DNA from the sample collection kit utilizing the DNA extraction kit provided with the CoVAST Test kit.

The laboratory can (or will) ship the extracted DNA to the CLIA laboratory.

Study Phase II: Primary Outcome (Days: 0, 7, 14, 21, 28):

1. For each subject, the PI or PI assistant can (or will) record the subject's severity of disease.
2. All information can (or will) be recorded in the appropriate CRF.

Inclusion Criteria

1. Male over the age of 18
2. First time present at the site
3. Laboratory confirmed SARS-CoV-2 infection
4. Able to give informed consent Exclusion Criteria 1. Unable to give informed consent
2. Diagnosed with an additional respiratory co-infection
3. XXY male Assessment of Efficacy Efficacy Parameters Severity of Disease Clinical assessment of disease severity can (or will) be made by attending physician and reported to the PI or PI assistant. Disease severity can (or will) be categorized as: discharged, hospitalization, admission to intensive care unit [ICU] or death.

Method and Timing

All assessments can (or will) be recorded on paper forms (CRFs) and stored with each subject's clinical study record.

The timing to complete the assessment of efficacy can (or will) be at Baseline, Day 7, Day 14, Day 21 and Day 28. After baseline assessment, the additional assessment can be performed by computerized hospital record search by the PI or PI assistant.

Primary Outcome Measures:

1. COVID Ordinal Outcomes Scale on Day 15 [Time Frame: assessed on study day 15]. The COVID Ordinal Scale for all patients can (or will) be determined on study day 15.

COVID Ordinal Scale can (or will) be defined as:

a. Death
b. Hospitalized on invasive mechanical ventilation or ECMO (extracorporeal membrane oxygenation)
c. Hospitalized on non-invasive ventilation or high flow nasal cannula
d. Hospitalized on supplemental oxygen
e. Hospitalized not on supplemental oxygen f. Not hospitalized with limitation in activity (continued symptoms)

g. Not hospitalized without limitation in activity (no symptoms)

Secondary Outcome Measures:

1. COVID Ordinal Outcomes Scale on Study Day 3 [Time Frame: assessed on study day 3]. The COVID Ordinal Scale for all patients can (or will) be determined on study day 3.

2. COVID Ordinal Outcomes Scale on Study Day 8 [Time Frame: assessed on study day 8]. COVID Ordinal Scale can (or will) be determined on study day 8.

3. Hospital-free days to Day 28 [Time Frame: 28 days]. This is defined as 28 days minus the number of days from randomization to discharge home. If a patient has not been discharged home prior to day 28 or dies prior to day 28, hospital free days will be zero.

Example 2

A double-blinded placebo controlled study was conducted on 97 male and female health care workers working at two hospital emergency room departments.

At baseline, all subjects were tested negative for SARS-CoV-2 infection. 50 subjects were given a daily dose of 10 mg/Kg/day oral cannabidiol. The reminder 47 subjects were given a placebo oral pill. At day 28 all subjects were tested for SARS-CoV-2 infection. Among the subjects that were administered the cannabidiol, 2 subjects were tested positive for SARS-CoV-2. Among the subjects administered the placebo, 9 subjects were tested positive for SARS-CoV-2.

Example 3

A double-blinded placebo controlled study was conducted on 28 male health care workers working at two hospital emergency room departments.

At baseline, all subjects were tested and found to be negative for SARS-CoV-2 infection. 18 subjects were given a daily dose of 750 mg/day oral flutamide. The reminder 10 subjects were given a placebo oral pill. At day 28 all subjects were tested again for SARS-CoV-2 infection. Among the subjects that were administered oral flutamide, 1 subject tested positive for SARS-CoV-2. Among the subjects administered the placebo, 3 subjects tested positive for SARS-CoV-2.

Example 4

A double-blinded placebo controlled study was conducted on 30 hospitalized male patients with average age of 61 years old.

All subjects were tested and found to be positive for SARS-CoV-2 infection. 15 subjects were assigned to enzalutamide treatment 160 mg qd. The other 15 subjects received standard treatment. Following 15 days of treatment, 20% of the subjects in the enzalutamide survived while 7% of the control group survived.

Example 5 a double-blinded placebo controlled study was conducted on 121 male health care workers working at two hospital emergency room departments.

At baseline, all subjects were tested and found to be negative for SARS-CoV-2 infection. 68 subjects were given a daily dose of 0.25 mg/day of oral dutasteride (Bis(trifluoromethyl)phenyl]-3-oxo-4-aza-5α-androst-1-ene-17β-carboxamide). The reminder 53 subjects were given a placebo oral pill. At day 28 all subjects were tested again for SARS-CoV-2 infection. Among the subjects that were administered oral dutasteride, 3 (4.4%) subject tested positive for SARS-CoV-2. Among the subjects administered the placebo, 9 (17%) subjects tested positive for SARS-CoV-2.

Example 6

A double-blinded placebo controlled study was conducted on 400 male patients with average age of 43.2 years old.

Patients were diagnosed with SARS-CoV-2 infection but were showing relatively mild symptoms. Patients were prescribed apalutamide 60 mg or a placebo and instructed to take 4 tablets daily. Patients were instructed to go home but return to the hospital if symptoms became worse. Efficacy parameters were defined as 1.) COVID-19 Diagnosis: COVID-19 positive diagnosis is defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization defined as confirmed hospitalization due to COVID-19, and 3.) Symptoms Severity of COVID-19 defined as symptoms severity of COVID-19 using Brescia-COVID Respiratory Severity Scale (BCRSS).

All subjects were tested and found to be positive for SARS-CoV-2 infection. All subjects were monitored for one month after the initiation of the therapy. 13 of 200 subjects in the apalutamide (240 mg) arm were admitted to the hospital after their first visit. The average BCRSS score for the 13 admitted patients was 3.2. 49 of 200 in the placebo group were admitted to the hospital with an average BCRSS score of 5.4.

Example 7 a double-blinded placebo controlled study was conducted on 113 hospitalized male patients with average age of 57 years old.

All subjects were tested and found to be positive for SARS-CoV-2 infection. 60 subjects were given an injection of cyproterone acetate (300 mg). The other 53 subjects received standard treatment. Following 15 days of treatment, 84% of the subjects in the cyproterone acetate survived while 64% of the control group survived.

Example 8

A double-blinded placebo controlled study was conducted on 340 male patients with average age of 39.2 years old.

Patients were diagnosed with SARS-CoV-2 infection but were showing relatively mild symptoms. Patients were divided into one of two arms. The treatment arm received a subcutaneous injection of degarelix (120 mg) at the start of the trial. Each group received tablets of bicalutamide (50 mg) or a placebo and were instructed to take 1 tablet daily. Patients were instructed to go home but return to the hospital if symptoms became worse. Efficacy parameters were defined as 1.) COVID-19 Diagnosis: COVID-19 positive diagnosis is defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization defined as confirmed hospitalization due to COVID-19, and 3.) Symptoms Severity of COVID-19 defined as symptoms severity of COVID-19 using Brescia-COVID Respiratory Severity Scale (BCRSS).

All subjects were tested and found to be positive for SARS-CoV-2 infection. All subjects were monitored for one month after the initiation of the therapy. 2 of 180 subjects in the bicalutamide plus degarelix arm were admitted to the hospital after their first visit. The average BCRSS score for the 2 admitted patients was 2.5. 31 of 160 in the placebo group were admitted to the hospital with an average BCRSS score of 6.2.

Example 9

A controlled study was conducted on 140 male patients with average age of 42.6 years old. Patients were diagnosed with SARS-CoV-2 infection but were showing relatively mild symptoms. Patients were divided into one of two arms. The treatment arm received a subcutaneous injection of degarelix (120 mg) at the start of the trial, the control arm received standard care. Patients were instructed to go home but return to the hospital if symptoms became worse. Efficacy parameters were defined as 1.) COVID-19 Diagnosis: COVID-19 positive diagnosis is defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization defined as confirmed hospitalization due to COVID-19, and 3.) Symptoms Severity of COVID-19 defined as symptoms severity of COVID-19 using Brescia-COVID Respiratory Severity Scale (BCRSS).

All subjects were tested and found to be positive for SARS-CoV-2 infection. All subjects were monitored for one month after the initiation of the therapy. 3 of 80 subjects in the degarelix arm were admitted to the hospital after their first visit. The average BCRSS score for the 2 admitted patients was 1.3. 12 of 60 subjects in the standard care group were admitted to the hospital with an average BCRSS score of 4.6.

Example 10

A double-blinded placebo controlled study was conducted on 25 male patients admitted to the hospital for complication resulting from flu with average age of 68.4 years old. Patients were diagnosed with Influenza A infection. Patients were divided into one of two arms. The treatment arm received a subcutaneous injection of degarelix (120 mg) at the start of the trial. Each group received 1 tablet of bicalutamide (50 mg) or a placebo daily. Patient progress was monitored by primary care physician. Efficacy parameters were defined as 1.) time to alleviation of fever 2.) mortality and length of hospital stay 3.) change in virus titer 48 hours after hospital admission.

All subjects were tested and found to be positive for Influenza A infection. 15 subjects were in the treatment group and 9 were in the placebo arm. Overall, the time to alleviation of fever was lower in the treated group compared with the control group [mean difference (MD), −7.17 hours; 95% confidence interval (CI) −11.00 to −3.34]. Mortality, length of hospital stay, change in virus titer 48 hours after admission, and the incidence of adverse events in these patients were not significantly different between the two groups.

Example 11

A double-blinded placebo controlled study was conducted on 36 male health care workers working at two hospital emergency room departments.

At baseline, all subjects were tested and found to be negative for SARS-CoV-2 infection. 18 subjects applied twice daily a topical ocular solution containing a low dosage finasteride. The reminder 18 subjects were given a placebo vehicle ocular solution. At day 28 all subjects were tested again for SARS-CoV-2 infection. Among the subjects that were administered finasteride, 1 subject tested positive for SARS-CoV-2. Among the subjects administered the placebo, 6 subjects tested positive for SARS-CoV-2.

Example 12

In-vitro Diagnostic Test to Guide Androgen Deprivation Therapy Dosage for COVID-19 Patients Investigational Device Device Name: COVID-19 Androgen Deprivation Therapy Dosage Selector (CoADTS)

Device Background:

COVID-19 Androgen Deprivation Therapy Dosage Selector (CoADTS) is a non-invasive In-Vitro Diagnostic device that utilizes qualitative DNA genotyping. CoADTS test requires a health care professional to collect a DNA sample using an FDA cleared DNA sample collection kit. The sample collection kit is an ORAcollectDx OCD-100A device manufactured by DNA Genotek, Inc (previously cleared under K152464). CoADTS test is intended to be performed at a Clinical Laboratory Improvement Amendments (CLIA) certified laboratory. The reagents used in performing the CoADTS test are manufactured in a GMP facility. CoADTS test reports the results of the DNA genotyping.

Trial Conduct

This study will be conducted in compliance with the protocol approved by the Institutional Review Board, and according to Good Clinical Practice standards. The CoADTS Test used in this study is manufactured according to GMP and the specimens will be analyzed at a CLIA laboratory. No deviation from the protocol will be implemented without the prior review and approval of the IRB except where it may be necessary to eliminate an immediate hazard to a research subject. In such case, the deviation will be reported to the IRB as soon as possible.

Population

This is a multi-center study to be conducted in at least 2 countries—Spain and the US. This exact protocol will be followed in each country. There will be a minimum of 2 separate sites and 2 separate PIs. In the US, the study will be approved by an IRB and in the other countries by the appropriate Ethics Committees.

The population for this study will be subjects recruited from each site (hospital).

Subjects will be males requesting a SARS-CoV-2 test following respiratory symptoms.

Subjects will be males 18 years and older of any ethnicity.

Trial Objectives

The primary purpose of this study is to determine the predictive value of the CoADTS Test. The predictive value will be calculated based on the positive percent agreement and negative percent agreement of the CoADTS Test. The results will be presented in 2×2 tables.

Trial Design
Primary Study Endpoints/Secondary Endpoints
Primary Outcome Measures:
Severity of Disease (discharged, hospitalization, admission to intensive care unit [ICU], and death) [Baseline, Day 7, Day 14, Day 21, Day 28]
Study Design/Type
This study is a prospective cross-sectional observational study. The study will have 4 arms:
Arm 1: Males first tested positive for SARS-CoV-2 at the site (hospital) with CAG length<24 (based on the CoADTS Test) and TMPRSS2 SNP (r58134378) positive (G)
Arm 2: Males first tested positive for SARS-CoV-2 at the site (hospital) with CAG length>=24 (based on the CoADTS Test) and TMPRSS2 SNP (r58134378) positive (G)
Arm 3: Males first tested positive for SARS-CoV-2 at the site (hospital) with CAG length<24 (based on the CoADTS Test) and TMPRSS2 SNP (r58134378) negative (A)
Arm 4: Males first tested positive for SARS-CoV-2 at the site (hospital) with CAG length>=24 (based on the CoADTS Test) and TMPRSS2 SNP (r58134378) negative (A)
Study Environment:
This is a multi-center study to be conducted in at least 2 countries—Spain and the US. This exact protocol will be followed in each country. There will be a minimum of 2 separate sites and 2 separate PIs. In the US, the study will be approved by an IRB and in the other countries by the appropriate Ethics Committees.
The study will be conducted at the site(s) listed above i.e., the PI's hospital. All data collection including sample collection will be performed at the site.
Study Design:
Study Phase Ia: Screening (First Site Visit)
The PI will screen each potential subject for the inclusion and exclusion criteria.
Study Phase Ib: Enrollment (First Site Visit)
Each qualified subject will complete and sign the informed consent form
Each subject will be assigned a subject study number
Study Phase Ic: Sample Collection (First Site Visit)
For each subject, the PI will collect the saliva DNA sample using the CoADTS Test Sample Collection Kit. The sample collection will be performed in accordance with IFU for the collection kit.
The sample collection kit will be sent to the hospital laboratory.
All information will be recorded in the appropriate CRFs.
Study Phase Id: Hospital Laboratory (First Site Visit)
The hospital laboratory will extract the DNA from the sample collection kit utilizing the DNA extraction kit provided with the CoADTS Test kit.
The laboratory will ship the extracted DNA to the CLIA laboratory
Study Phase II: Primary Outcome (Days: 0, 7, 14, 21, 28):
1. For each subject, the PI or PI assistant will record the subject's severity of disease
2. All information will be recorded in the appropriate CRFs
Inclusion Criteria
Male over the age of 18
First time present at the site
Laboratory confirmed SARS-CoV-2 infection
Able to give informed consent
Exclusion Criteria
Unable to give informed consent
Diagnosed with an additional respiratory co-infection
XXY males Assessment of Efficacy
Efficacy Parameters
Severity of Disease
Clinical assessment of disease severity will be made by attending physician and reported to the PI or PI assistant. Disease severity will be categorized as: discharged, hospitalization, admission to intensive care unit [ICU] or and death.
Method and Timing
All assessments described in section 5.1 will be recorded on paper forms
(CRFs) and stored with each subject's clinical study record.
The timing to complete the assessment of efficacy will be at Baseline, Day 7, Day 14, Day 21 and Day 28. After baseline assessment, the additional assessment can be performed by computerized hospital record search by the PI or PI assistant.

Example 13

A controlled study was conducted on 100 male patients with average age of 48.3 years old. Patients were diagnosed with SARS-CoV-2 infection but were showing relatively mild symptoms. Patients were divided into one of two arms. The treatment arm was prescribed bicalutamide (50 mg) once daily at the start of the trial, the control arm received standard care. Patients were instructed to go home but return to the hospital if symptoms became worse. Efficacy parameters were defined as 1.) COVID-19 Diagnosis: COVID-19 positive diagnosis were defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization was defined as confirmed hospitalization due to COVID-19, and 3.) Symptoms Severity of COVID-19 was defined as symptoms severity of COVID-19 using Brescia-COVID Respiratory Severity Scale (BCRSS).
All subjects were tested and found to be positive for SARS-CoV-2 infection. All subjects were monitored for one month after the initiation of the therapy. 6 of 50 subjects in the bicalutamide arm were admitted to the hospital after their first visit. The average BCRSS score for the 6 admitted patients was 1.9. 17 of 50 subjects in the standard care group were admitted to the hospital with an average BCRSS score of 4.1.

Example 14

A controlled study was conducted on 40 male patients with average age of 41.6 years old. Patients were diagnosed with SARS-CoV-2 infection but were showing relatively mild symptoms. Patients were divided into one of two arms. The treatment arm was prescribed darolutamide (300 mg) orally twice daily at the start of the trial, the control arm received standard care. Patients were instructed to go home but return to the hospital if symptoms became worse. Efficacy parameters were defined as 1.) COVID-19 Diagnosis: COVID-19 positive diagnosis was defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization was defined as confirmed hospitalization due to COVID-19, and 3.) Symptoms Severity of COVID-19 was defined as symptoms severity of COVID-19 using Brescia-COVID Respiratory Severity Scale (BCRSS).

All subjects were tested and found to be positive for SARS-CoV-2 infection. All subjects were monitored for one month after the initiation of the therapy. 1 of 20 subjects in the darolutamide arm was admitted to the hospital after their first visit. The patient's BCRSS score was 2. 3 of 20 subjects in the standard care group were admitted to the hospital with an average BCRSS score of 3.6.

Example 15

A controlled study was conducted on 150 male patients with average age of 45.7 years old. Patients were diagnosed with SARS-CoV-2 infection but were showing relatively mild symptoms. Patients were divided into one of two arms. The treatment arm was prescribed abiraterone (500 mg) twice daily at the start of the trial, the control arm received standard care. Patients were instructed to go home but return to the hospital if symptoms became worse. Efficacy parameters were defined as 1.) COVID-19 Diagnosis: COVID-19 positive diagnosis was defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization was defined as confirmed hospitalization due to COVID-19, and 3.) Symptoms Severity of COVID-19 was defined as symptoms severity of COVID-19 using Brescia-COVID Respiratory Severity Scale (BCRSS).

All subjects were tested and found to be positive for SARS-CoV-2 infection. All subjects were monitored for one month after the initiation of the therapy. 4 of 75 subjects in the abiraterone arm were admitted to the hospital after their first visit. The patients average BCRSS score was 1.8. 15 of 75 subjects in the standard care group were admitted to the hospital with an average BCRSS score of 4.7.

Example 16

A controlled study was conducted on 90 male patients with average age of 51 years old. Patients were diagnosed with SARS-CoV-2 infection but were showing relatively mild symptoms. Patients were divided into one of two arms. The treatment arm was prescribed nilutamide (300 mg) orally once daily at the start of the trial, the control arm received standard care. Patients were instructed to go home but return to the hospital if symptoms became worse. Efficacy parameters were defined as 1.) COVID-19 Diagnosis: COVID-19 positive diagnosis was defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization was defined as confirmed hospitalization due to COVID-19, and 3.) Symptoms Severity of COVID-19 defined as symptoms severity of COVID-19 using Brescia-COVID Respiratory Severity Scale (BCRSS).

All subjects were tested and found to be positive for SARS-CoV-2 infection. All subjects were monitored for one month after the initiation of the therapy. 3 of 50 subjects in the nilutamide arm were admitted to the hospital after their first visit. The patients BCRSS score was 1.3. 8 of 40 subjects in the standard care group were admitted to the hospital with an average BCRSS score of 4.0.

Example 17

A controlled study was conducted on 16 male patients with average age of 64 years old. Patients were diagnosed with SARS-CoV-2 infection but were showing relatively mild symptoms. Patients were divided into one of two arms. The treatment arm received docetaxel 75 mg/m2 IV over 1 hour at the start of the trial, the control arm received standard care. Patients were instructed to go home but return to the hospital if symptoms became worse. Efficacy parameters were defined as 1.) COVID-19 Diagnosis: COVID-19 positive diagnosis was defined as subject exhibiting symptoms of acute respiratory infection, defined as one or more of the following cough, fever (>37.5° C./99.5° F.), shortness of breath, sore throat, and a positive SARS-CoV-2 rtPCR test 2.) COVID-19 Hospitalization defined as confirmed hospitalization due to COVID-19, and 3.) Symptoms Severity of COVID-19 was defined as symptoms severity of COVID-19 using Brescia-COVID Respiratory Severity Scale (BCRSS).

All subjects were tested and found to be positive for SARS-CoV-2 infection. All subjects were monitored for one month after the initiation of the therapy. 0 of 8 subjects in the docetaxel arm were admitted to the hospital after their first visit. 2 of 8 subjects in the standard care group were admitted to the hospital with an average BCRSS score of 4.5.

It should be noted that the dosage used in administering embodiments of the compositions can be low and still be effective. A low dosage can be within a range from 1/10× to 1× of the following exemplary dosages listed:

topical skin application of finasteride at 10% (w/w)
oral finasteride at 0.1-10 mg
dutasteride at 0.1 mg/day to 1.0 mg/day
degarelix at 240 mg
oral cannabidiol at 10/mg/Kg/day
oral flutamide at 750 mg/day
enzalutamide at 160 mg qd
oral dutasteride at 0.25 mg/day
apalutamide at 60 mg 4 times per day
injection of cyproterone acetate (300 mg).
subcutaneous injection of degarelix (120 mg)
bicalutamide at 50 mg per day
subcutaneous injection of degarelix (120 mg)
oral darolutamide at 300 mg twice daily
abiraterone at 500 mg twice daily
oral nilutamide at 300 mg once daily
docetaxel at 75 mg/m2 IV over 1 hour However, dosages within a range from 1/10× to 3× of the above identified dosages can be used. Thus, dosages can be within a range from:

topical skin application of finasteride at 1-30% (w/w)
oral finasteride at 0.01-30 mg
dutasteride at 0.1 mg/day to 3.0 mg/day
degarelix at 24 mg-720 mg
oral cannabidiol at 1-30/mg/Kg/day
oral flutamide at 75-2,250 mg/day
enzalutamide at 16-480 mg qd
oral dutasteride at 0.025-0.75 mg/day
apalutamide at 6-180 mg 4 times per day
injection of cyproterone acetate (30-900 mg).
subcutaneous injection of degarelix (12-360 mg)
bicalutamide at 5-150 mg per day
subcutaneous injection of degarelix (12-360 mg)
oral darolutamide at 30-900 mg twice daily
abiraterone at 50-1500 mg twice daily
oral nilutamide at 30-900 mg once daily
docetaxel at 7.5-225 mg/m2 IV over 1 hour

The invention claimed is:

1. A composition for treatment of a viral respiratory infection by reducing viral entry in a lung, the composition comprising:
   (i) an androgen receptor antagonist or an anti-androgen, wherein the androgen receptor antagonist or the anti-androgen blocks production of proteins in the lung via decreasing an amount of TMRRSS2 expression and the androgen receptor antagonist or the anti-androgen is selected from the group consisting of flutamide, bicalutamide, nilutamide, topilutamide, enzalutamide, apalutamide, seviteronel, aminoglutethimide, darolutamide, proxalutamide and a combination thereof; and
   (ii) a glucocorticoid.

2. The composition of claim 1, wherein the viral respiratory infection is any one or combination of coronavirus, influenza, influenza A, influenza B, SARS-CoV-1, SARS-CoV-2, MERS-CoV, or rhinovirus.

3. The composition of claim 1, wherein the androgen receptor antagonist or the anti-androgen is combined with any one or combination of an anti-inflammatory agent, an anti-bacterial agent, or aspartame.

4. The composition of claim 1, wherein the composition is formulated for use as a treatment of the viral respiratory infection, a therapy for the viral respiratory infection, a prophylactic for the viral respiratory infection, and/or a preventive measure for contracting the viral respiratory infection.

5. The composition of claim 4, wherein the composition is further formulated for use as a treatment for prostate cancer, castration-resistant prostate cancer, metastatic castration-sensitive prostate cancer, non-metastatic castration-resistant prostate cancer and/or benign prostatic hyperplasia.

6. A method of treating a patient having or suspected of having a viral respiratory infection, the method comprising:
   administering a composition to the patient, the composition including any one or combination of:
   (i) an androgen receptor antagonist or anti-androgen, wherein the androgen receptor antagonist or the anti-androgen is selected from the group consisting of flutamide, bicalutamide, nilutamide, topilutamide, enzalutamide, apalutamide, seviteronel, aminoglutethimide, darolutamide, proxalutamide and a combination thereof; and
   (ii) a glucocorticoid.

7. The method of claim 6, wherein the administration of the composition involves any one or combination of topical application to the skin, nasal application, sublingual application, oral application, via injection, via inhalation, or ocular application.

8. The method of claim 6, wherein the viral respiratory infection is any one or combination of coronavirus, influenza, influenza A, influenza B, SARS-CoV-1, SARS-CoV-2, MERS-CoV or rhinovirus.

9. The method of claim 6, wherein the composition is used as a treatment for the viral respiratory infection, a therapy for the viral respiratory infection, a prophylactic for the viral respiratory infection, and/or a preventive measure for contracting the viral respiratory infection.

10. The method of claim 6, wherein the treatment involves administering the composition as a treatment for the viral respiratory infection and/or a prophylactic for the viral respiratory infection before, during, and/or after the patient is first diagnosed with the viral respiratory infection and/or before, during, and/or after the patient is hospitalized due to the viral respiratory infection.

11. The method of claim 9, wherein the composition is further used as a treatment for prostate cancer, castration-resistant prostate cancer, metastatic castration-sensitive prostate cancer, non-metastatic castration-resistant prostate cancer and/or benign prostatic hyperplasia.

12. The method of claim 6, further comprising predicting anti-androgen treatment response via evaluation of genetic variation in the gene and/or promotor region of the androgen receptor (AR).

13. The method of claim 12, further comprising guiding selection of anti-androgen treatment and/or dosage selection of the selected anti-androgen treatment based on the predicted anti-androgen treatment response.

14. The method of claim 12, wherein predicting the anti-androgen treatment response involves measuring polymorphisms in the AR gene.

15. The method of claim 12, wherein:
   the number of cytosine-adenine-guanine (CAG) repeats in the first exon of the AR gene, the number of guanine-guanine-(any nucleotide) (GGN) repeats in the first exon in the AR gene, and/or a ratio of CAG/GGN repeats is used as the genetic variant; and
   a cut off value for the number of CAG repeats the first exon of AR gene is used to define a person with androgen sensitivity.

16. The method of claim 15, wherein the cut-off value for the number of CAG repeats the first exon of AR gene is between 10 and 30.

17. The method of claim 12, wherein variants in the promoter region of the AR are used as the genetic variant.

18. The method of claim 6, wherein the anti-androgen is combined with any one or combination of an anti-inflammatory agent, an anti-bacterial agent, or aspartame.

19. The method of claim 18, wherein the viral respiratory infection is SARS-CoV-2.

20. The method of claim 6, wherein administering the composition involves administering:
   topical skin application of finasteride at 1-30% (w/w), oral finasteride at 0.01-30 mg, dutasteride at 0.1 mg/day to 3.0 mg/day, degarelix at 24 mg-720 mg, oral cannabidiol at 1-30/mg/Kg/day, oral flutamide at 75-2, 250 mg/day, enzalutamide at 16-480 mg qd, oral dutasteride at 0.025-0.75 mg/day, apalutamide at 6-180 mg 4 times per day, injection of 30-900 mg of cyproterone acetate, subcutaneous injection of 12-360 mg of degarelix, bicalutamide at 5-150 mg per day, subcutaneous injection of 12-360 mg of degarelix, oral darolutamide at 30-900 mg twice daily, abiraterone at 50-1500 mg twice daily, oral nilutamide at 30-900 mg once daily, or docetaxel at 7.5-225 mg/m2 IV over 1 hour.

21. The method of claim 6, wherein administering the composition involves administering:
   topical skin application of finasteride at 1-10% (w/w), oral finasteride at 0.1-10 mg, dutasteride at 0.1 mg/day to 1.0 mg/day, degarelix at 24 mg-240 mg, oral cannabidiol at 1-10/mg/Kg/day, oral flutamide at 75-750 mg/day, enzalutamide at 16-160 mg qd, oral dutasteride at 0.025-0.25 mg/day, apalutamide at 6-60 mg 4 times per day, injection of 30-300 mg of cyproterone acetate, subcutaneous injection of 12-120 mg of degarelix, bicalutamide at 5-50 mg per day, subcutaneous injection of 12-120 mg of degarelix, oral darolutamide at 30-300 mg twice daily, abiraterone at 50-500 mg twice daily, oral nilutamide at 30-300 mg once daily, or docetaxel at 7.5-750 mg/m2 IV over 1 hour.

22. A method of treating a patient having or suspected of having a viral respiratory infection, the method comprising:
  determining the risk of severity or mortality of the viral respiratory infection for the patient by identifying and measuring genetic variation in the gene and/or promotor region of any one or combination of the androgen receptor (AR), TMPRSS2, furin, or ACE2; and
  selecting a composition and a dosage for the composition based on the determined risk of severity or mortality;
  administering the composition to the patient, the composition including any one or combination of:
    an androgen receptor antagonist or anti-androgen, wherein the androgen receptor antagonist or the anti-androgen is selected from the group consisting of flutamide, bicalutamide, nilutamide, topilutamide, enzalutamide, apalutamide, seviteronel, aminoglutethimide, darolutamide, proxalutamide and a combination thereof; and
    a glucocorticoid.

23. The method of claim 22, wherein the method involves use of a kit, wherein:
  a genetic sample via buccal swab, saliva sample, blood sample, tissue sample, and/or hair sample is obtained via a deoxyribonucleic acid (DNA) sample collection unit;
  polymorphisms in the androgen receptor gene are identified via a viral respiratory infection sensitivity unit; and
  an assay analysis is performed using a DNA diagnostic assay.

24. The method of claim 22, further comprising:
  predicting anti-androgen treatment response via evaluation of a genetic variation in the gene and/or promotor region in any one or combination of AR, TMPRSS2, furin, or ACE2.

25. The method of claim 24, wherein the genetic variation includes any one or combination of:
  one or more of: F877L/T878A, F877L, T878A, rs137852591, rs104894742, rs1057518177, rs1057521121, rs1057521122, rs1057523747, rs1064793480, rs1064793645, rs1064794065, rs1064794069, rs1064795250, rs1085307685, rs1085307962, rs12014709, rs1204038, rs1337080, rs137852562, rs137852563, rs137852564, rs137852565, rs137852566, rs137852567, rs137852568, rs137852569, rs137852570, rs137852571, rs137852572, rs137852573, rs137852574, rs137852575, rs137852576, rs137852577, rs137852578, rs137852579, rs137852580, rs137852581, rs137852582, rs137852583, rs137852584, rs137852585, rs137852586, rs137852587, rs137852588, rs137852589, rs137852590, rs137852592, rs137852593, rs137852594, rs137852595, rs137852596, rs137852597, rs137852598, rs137852599, rs137852600, rs137852601, rs1800053, rs201934623, rs2361634, rs5031002, rs5918757, rs6152, rs6624304, rs750324117, rs754201976, rs755226547, rs759327087, rs864622007, rs869320731, rs869320732, rs878853033, rs886039558, rs886041050, rs886041128, rs886041129, rs886041130, rs886041131, rs886041132, rs886041133, rs886041352, rs9332969, or rs9332971;
  one or more of: rs12329760, rs2070788, rs383510, rs463727, rs34624090, rs55964536, rs734056, rs4290734, rs34783969, rs11702475, rs35899679, rs35041537, rs8134378, rs2070788, rs9974589, rs7364083, or rs2070788;
  one or more of: rs2285666, G8790A, rs35803318, rs1978124, rs2048683, rs2074192, rs2106809, rs2285666, rs233575, rs4240157, rs4646155, rs4646156, rs4646174, rs4646176, rs4646188, rs6632677, rs714205, or rs879922; or
  one or more of: rs17514846, rs2071410, rs4702, rs4932178, rs6226, or rs6227.

* * * * *